US012371738B2

(12) United States Patent
Gilbert et al.

(10) Patent No.: US 12,371,738 B2
(45) Date of Patent: Jul. 29, 2025

(54) MICROFLUIDIC PLATFORM AND A METHOD FOR ELECTROSTATICALLY-ENHANCED, EXCITATION-MODULATED REVERSE TRANSCRIPTASE QUANTITATIVE POLYMERASE CHAIN REACTION ANALYSIS

(71) Applicant: VERITAS DIAGNOSTIC LLC, New York City, NY (US)

(72) Inventors: Martyn Neil Gilbert, Cambridge (GB); Peter Hornick, New York City, NY (US)

(73) Assignee: VERITAS DIAGNOSTIC LLC, New York City, NY (US)

( * ) Notice: Subject to any disclaimer, the term of this patent is extended or adjusted under 35 U.S.C. 154(b) by 947 days.

(21) Appl. No.: 17/511,407

(22) Filed: Oct. 26, 2021

(65) Prior Publication Data
US 2022/0127668 A1  Apr. 28, 2022

Related U.S. Application Data

(60) Provisional application No. 63/105,780, filed on Oct. 26, 2020.

(51) Int. Cl.
*C12Q 1/68* (2018.01)
*B01L 3/00* (2006.01)
(Continued)

(52) U.S. Cl.
CPC ...... *C12Q 1/6851* (2013.01); *B01L 3/502715* (2013.01); *B01L 3/50273* (2013.01);
(Continued)

(58) Field of Classification Search
CPC ..... C12Q 1/6851; C12Q 1/686; B01L 3/5457; B01L 7/52; B01L 3/502715; B01L 3/502; B01L 3/50273
(Continued)

(56) References Cited

U.S. PATENT DOCUMENTS

2006/0239861 A1  10/2006  Higashino et al.
2011/0124098 A1   5/2011  Rose et al.
(Continued)

OTHER PUBLICATIONS

White, A. K. et al, Proceedings of the National Academy of Sciences 2011, 108, 13999-14004. (Year: 2011).*
(Continued)

*Primary Examiner* — Arlen Soderquist
(74) *Attorney, Agent, or Firm* — Maschoff Brennan

(57) ABSTRACT

A reverse transcriptase quantitative polymerase chain reaction based analyzing system includes a sampling tube. The sampling tube includes a tube portion, a cap coupled to the tube portion via a ratchet locking mechanism. The system comprises a microfluidic processing unit coupled to the sampling tube. An intake system receives pre-registered, sealed microfluidic labs into the system, and disinfects them before processing begins. The microfluidic processing unit comprises a piezo electric type ribonucleic acid extraction and concentration unit coupled to the sampling tube, an eluent storage unit, an eluate dosing chamber, an analysis settling chamber with a bubble removal area, an assay rehydration unit, an assay analysis unit and a no-target control analysis unit.

20 Claims, 26 Drawing Sheets

(51) Int. Cl.
*C12Q 1/6851* (2018.01)
*C12Q 1/686* (2018.01)

(52) U.S. Cl.
CPC ............ *B01L 3/5457* (2013.01); *C12Q 1/686* (2013.01); *B01L 2300/021* (2013.01); *B01L 2300/042* (2013.01); *B01L 2300/0645* (2013.01); *B01L 2300/0654* (2013.01); *B01L 2300/18* (2013.01); *B01L 2400/0415* (2013.01); *B01L 2400/0439* (2013.01); *B01L 2400/082* (2013.01)

(58) Field of Classification Search
USPC .......................................................... 422/527
See application file for complete search history.

(56) References Cited

U.S. PATENT DOCUMENTS

| | | | | |
|---|---|---|---|---|
| 2012/0115738 | A1* | 5/2012 | Zhou | B01F 33/30 435/6.12 |
| 2014/0174926 | A1* | 6/2014 | Bort | B01F 33/3021 204/601 |
| 2017/0283859 | A1 | 10/2017 | Lin et al. | |
| 2018/0214878 | A1* | 8/2018 | Chang | A61B 5/150832 |
| 2019/0017629 | A1 | 1/2019 | Laser et al. | |
| 2019/0284612 | A1 | 9/2019 | Buse et al. | |

OTHER PUBLICATIONS

Harb, W. et al, Translational Oncology 2013, 6, 528-538. (Year: 2013).*
Lim, G. S. et al, Lab on a Chip 2015, 15, 4032-4043. (Year: 2015).*
Ramshani, Z. et al, Communications Biology 2019, 2, article 189, 9 pages. (Year: 2019).*
PCT International Search Report and Written Opinion issued in corresponding application No. PCT/US2021/056697, dated Jan. 27, 2022.

* cited by examiner

MICROFLUIDIC PLATFORM AND A METHOD FOR ELECTROSTATICALLY-ENHANCED, EXCITATION-MODULATED REVERSE TRANSCRIPTASE QUANTITATIVE POLYMERASE CHAIN REACTION ANALYSIS

TECHNICAL FIELD

The present disclosure generally relates to polymerase chain reaction analysis, and more particularly relates to reverse transcriptase quantitative polymerase chain reaction analysis undertaken in a microfluidic platform. The disclosure also has application to loop-mediated isothermal amplification (LAMP) analysis performed in conjunction with a microfluidic platform.

BACKGROUND

Viruses invade host cells. Using the host as a source of material for reproduction, viruses replicate, emerging from the host cell and sometimes killing the cell. Viruses are known to cause diseases that can be epidemic or pandemic, for example, but not limited to AIDS and SARS-COV2, or even tumors. The most common technique to detect virus is the reverse transcriptase quantitative polymerase chain reaction (RT-qPCR). RT-qPCR involves a first stage of reverse transcription of RNA into complimentary DNA (cDNA) and a second stage of amplification of specific DNA targets using a real time PCR, also called quantitative PCR (qPCR), wherein amplification reaction is monitored using fluorescence. qPCR is used in a wide range of medical, agricultural, and forensic applications. Many pathogenic microorganisms, including some viruses, bacteria, parasites, and fungi that cause infectious diseases and can be identified using PCR, aiding diagnosis, and treatment. PCR is also used for genotyping to detect several diseases, and for nutrigenomics to detect food intolerance.

Existing technique of qPCR is based on 96-well plates, each carrying a test sample plus a combination of test reagents. Samples can be processed in 96 well plates, 384, 768 or 1536 well plates. As the number of sample size increases, so does the variation in sample processing and the results from the tests. Variations can be due to multiple factors, for example, due to contamination or due to human error. If there is high variation between triplicates of the same samples, the interpretation can be difficult, and may affect the outcome of the experiment or diagnostics. So, reducing the variation between samples of the same type is critical to the confidence in the interpretation. These variations result in false positives or false negatives. It is known that, with the qPCR technique, the chances of test results being a false negative or a false positive are high if one or more contaminants, reaction inhibitors, or sample acquisition errors are present. A false negative test result can result in an infected person transmitting the pathogen into many other people unknowingly, while a false positive test result can result in a non-infected person being treated for the disease when it is not required. Further, a false positive result can result in restricting the non-infected person as well as the people in contact with the non-infected person from carrying out with their normal daily routines. Furthermore, the qPCR technique based on 96-well trays is a time-consuming process and test results are not readily available to a person. There is a prolonged duration from when the sample is given for testing till the test results are declared. This poses the risk of an infected person transmitting to other people during this duration.

Typically, qPCR systems require the human samples to be taken at one location and then transported to another location to be analyzed. The chances of the samples being contaminated during collection, degraded during transport from one location to another (for example, though excessive temperature), or from the sampling tube to the analyzer, are high. There are multiple steps from sampling tube to the analyzer: Samples must go through a lengthy pre-processing system in a laboratory environment, in which the samples are removed from a sampling tube within a secure biocontainment booth and moved through a series of steps that frequently includes RNA extraction, eluent wash, cDNA conversion, mixing with reagents and gene-selective primers and detection probes, and finally placement into the well plates for qPCR. Each of these steps creates risks for contamination. Amongst the most challenging risks for PCR is that a single contaminant molecule conveyed by aerosol from another test or via the commonly used micro pipetting techniques may be sufficient to prevent a given test from producing the correct result.

Though qPCR can be based on 96 well plates, 384, 768 or 1536 well plates, during a pandemic, existing qPCR analyzers are insufficient and not scalable considering the large volumes of samples needed to be analyzed. Further, qPCR systems need to be operated by trained technicians in a biologically secure laboratory setting and cannot be deployed within workspaces, in waiting areas prior to boarding planes, buses, theaters, sporting events, religious centers, schools, etc. Moreover, existing products offering utility in non-laboratory settings are restricted to small quantities of simultaneous tests, typically between one and sixteen at a time. This is a considerable restriction in settings such as airports and other transportation hubs as well as locations that have highly unequal rates of movement of people where the average rate of tests done a day, is dissimilar to the peak traffic flow required. Furthermore, the reagent volume required in conventional qPCR tests is 1-10 microliters per sample, and the cost of this volume of reagents is typically a significant component of the total testing cost.

Each qPCR system has, by virtue of its design and the selected reagents and polymers, a lower limit of detection ("LoD") below which the system cannot detect disease. This limit in existing systems is typically 100-500 copies of the pathogen per sample. Further, the loop-mediated isothermal amplification (LAMP) analysis is not well suited to accurately detect pathogens in early, pre-symptomatic or asymptomatic individuals where the copy count may be one or two orders of magnitude lower.

There is an unmet need for a system and method for detecting viruses during pandemics or epidemics, a system that is scalable, capable of giving accurate results with much lower false negative and false positive rates, capable of detecting disease earlier by virtue of a lower LoD, minimum human intervention so that there is less human error and less scope of contamination, capable of deployable in public places, and capable of giving test results faster and at an affordable cost.

SUMMARY

To eliminate the abovementioned disadvantages, the primary object of the present disclosure is to provide a microfluidic platform and a method for detecting any given virus using the reverse transcriptase quantitative polymerase chain reaction (RT-qPCR) technique. The system will also have application for a range of PCR tests in medical and agricultural settings. In particular, and as its first application, the microfluidic platform is used to detect SARS-COV2 virus from human saliva sample using RT-qPCR analysis.

The microfluidic platform includes a sampling tube and a microfluidic laboratory (MFL), and optical subsystems. In one embodiment of the present disclosure, the sampling tube is used separately to collect the saliva sample and can be coupled to the MFL for analysis. In another embodiment of the present disclosure, the sampling tube is integrated with the MFL as a single unit. The MFL is provided with acoustic motors and acoustic valves to sequence the flow of the saliva in an added medium for further processing. The MFL includes an RNA extraction and concentration chamber, an eluate dosing chamber, a settling chamber, bubble removal chambers, and an analysis master mix chamber. The MFL includes reservoirs for holding various reagents in liquid form or powder form. Important attributes of the integrated embodiment are further reduced opportunities for contamination as the sampling tube and MFL are manufactured as one in a factory setting equal to or better than pharmaceutical-grade surface and environmental controls. Additionally, the integrated embodiment avoids the need for human or robotic systems to clean and join the sampling tube with the MFL or transfer the sampling tube contents to the MFL with the risk of aerosol contamination that entails.

It is an object of the present disclosure to provide the MFL having two coins, being the name given to the reaction chambers, one being an assay coin and the other a no-target control coin. Coins are assembled to include temperature sensors, a mirror, and a lens mechanism. In the analytical instrument, they will be subjected to a well-controlled temperature which in one or more embodiments is provided by a heat pump in order the coins may be heated or cooled. Essentially, coins are reaction chambers where a master mix of various reagents, mix with the eluate having the extracted RNA. In one embodiment, to detect SARS-COVID2 virus, the master mix of reagents includes reverse transcriptase enzyme, taq polymerase enzyme, PCR primer, and one or more dyes that emits fluorescence. As can be appreciated, the mix of reagents can vary depending on the pathogen that is being sought, and a given pathogen may be analyzed with a range of reagents that target different sequences with the target genome. If an RNA-based pathogen is present, the mixing of the reagents with the eluate containing RNA, causes reverse transcription of RNA into cDNA. Further, using qPCR, the coins provide amplification of specific DNA target sequences within the genome.

The optical subsystems surrounding the coins primarily include one or more light sensors for example CMOS or CCD linear arrays or area imagers, excitation sources for example light emitting diodes (LEDs), filters, and a mirror integrated to the coins. The photo detectors detect the emission from the coins. Successive images are captured and correspond to different excitation spectra and sequential thermocycle iterations. It is another object of the present disclosure to reduce noise in the microfluidic platform. Noise reduction includes electrical, electronic, optical, and biological noise reduction. The optical subsystems are designed to reduce the noises and improve the signal to noise ratio. An improved signal to noise ratio and improved optics are critical factors in facilitating lower limits of detection and lower false negative rates.

In one embodiment, a reverse transcriptase quantitative polymerase chain reaction based analyzing system comprises a sampling tube. The sampling tube comprises a tube portion, a cap coupled to the tube portion via a ratchet locking mechanism, wherein the cap comprises a closure optical detection pattern, and a radio frequency identification (RFID) tag disposed between the cap and the tube portion. The system includes a microfluidic processing unit coupled to the sampling tube, wherein the microfluidic processing unit comprises a piezo electric type ribonucleic acid extraction and concentration unit coupled to the sampling tube via a plurality of sample flow control devices, an eluent storage unit coupled to the piezo electric type ribonucleic acid extraction and concentration unit via a plurality of eluent flow control devices, an eluate dosing chamber coupled to the piezo electric type ribonucleic acid extraction unit via a plurality of eluate flow control devices, an analysis settling chamber coupled to the eluate dosing chamber, an assay rehydration unit coupled to the analysis settling chamber via a plurality of assay control devices, an assay analysis unit coupled to the analysis settling chamber and a no-target control analysis unit coupled to the assay rehydration unit for the purposes of applying a negative control to the biological assay and simultaneously calibrating the optical metrology system by the provision of passive dyes that will be present in effectively the same quantities in both the no-target control and the biological sample, wherein use of lyophilization in factory to leave the required reagents in the allocated chambers of the microfluidic laboratory or microfluidic processing unit, wherein the final stage of preparation prior to calibration involves displacing the air in the channels and chambers by argon in order to dispel oxygen that might otherwise facilitate gradual deterioration in the regents by oxidation. Within this embodiment the purpose of the RFID tag within the cap is to facilitate rapid central laboratory use of the system. Within central laboratories, valuable time is lost wherein skilled technicians must open shipping envelopes or other containers in a biologically secure environment in case the sampling tube within has not been properly closed, and pathogens have contaminated the inner volume of the shipping envelopes or containers.

In another embodiment, a method for analyzing a biological sample, using a reverse transcriptase quantitative polymerase chain reaction analyzing system includes receiving a sample within a tube portion of a sampling tube, coupling a cap of the sampling tube to the tube portion via a ratchet locking mechanism, depositing a microfluidic laboratory comprising the sampling tube in an analytic cell (AC), wherein AC is an analytical process environment, wherein the AC may be just a single unit or may be one of a number assembled in a row; wherein a row of ACs, known as a RandOm-Access Analytical (RoaaaR) Array may be a singular unit or may be one of many housed within an outer chassis, wherein the deposition is by way of either manual insertion or robotic assignment of individual sampling tubes and microfluidic laboratories into vacant ACs; wherein asynchronous, simultaneous processing of sampling tubes integrated with microfluidic laboratories whereby each sample test commences as soon as it is inserted into an AC; wherein a control system to maintain asynchronism between assays in progress such that the optical metrology system is kept in constant use without delaying any given assay; wherein a signal detection mechanism using modulation of the excitation light correlated with both the spectrum and the intensity of individual wavelengths in the emission spectra to reduce electrical, electronic, optical and biological noise; wherein use of same modulation of the excitation light as a means of multiplexing by way of time division multiplexing (TDM) emissions from two or more ACs to economically use the same optical metrology system. The method includes checking, by a detection sensor, a locking of the cap to the tube portion, mixing a lysis buffer with the sample within the sampling tube to generate a lysated sample within the sampling tube via a mixing unit, circulating the lysated sample from the sampling tube to a piezo electric type element, electrostatic ribonucleic acid extraction and concentration unit via a plurality of sample flow control devices, separating ribonucleic acid strands from the lysated sample within the piezo electric type element, electrostatic ribonucleic acid extraction and concentration unit, circulating an eluent between an eluent storage unit and the piezo electric type element, electrostatic ribonucleic acid extraction and concentration unit, extracting the separated ribonucleic acid strands, using the eluent from the piezo electric type element, electrostatic ribonucleic acid extraction unit and transferring an eluate comprising the extracted ribonucleic acid strands to an analysis settling chamber via an eluate dosing chamber and a plurality of eluate flow control devices, mixing a portion of master mixture from an assay rehydration unit with the eluate within the analysis settling chamber, transferring a first portion of the master mixture and the eluate to an assay analysis unit to analyze mixture of the portion of the master mixture and the eluate to diagnose a biological condition associated with the sample, transferring a second portion of the master mixture from the assay rehydration unit to a no-target control analysis unit to perform a no-target control analysis of the second portion of the master mixture, performing uniform (isothermal) or varying temperature control of the reverse transcriptase, quantitative polymerase chain reaction (RT-qPCR) assay or any other assay chemistry benefitting from the high accuracy, contaminant-free, optical detection methods, providing asynchronous processing of the collection of simultaneous assays in a system to minimize the test extraction periods and share the more costly resources such as the optical subsystem between assays without slowing individual assays and equipping individual microfluidic laboratories with mirrors underneath their reaction chambers to maximize the available emitted fluorescence, approximately doubling the light at each stage and for qPCR or RT-qPCR, reducing the cycle count by one.

In another embodiment, a closed loop method of quality control of reverse transcriptase quantitative polymerase chain reaction analyzing system or any other chemistry undertaking biological assays whereby calibration data of the both the individual consumables and the measuring instrument are obtained and used. The method includes obtaining calibration data in the controlled environment of a purpose-designed manufacturing facility or the adaption of an existing one such as a pharmaceutical manufacturing facility, filling the individual consumables and sealing them within the controlled environment of the factory, storing the calibration data in both a non-volatile store that is a permanent component or attribute of the consumables and also storing it in an Internet-connected 'cloud' data storage facility such that the calibration data is obtainable for a specific consumable both locally in the test instrument and by way of quality control also to analytic systems such that parametric variation of the consumables and instrument may be compensated and corrected at the time of assay execution, and the closed environment of the consumables which excludes both contaminant ingress and pathogen egress as well as rendering harmless any pathogens in their volume and on their surface facilitates use without the attendance of clinically or scientifically-trained operatives permitting use in any environment and by any persons including the patients or clients themselves thus permitting the widest application and accessibility.

In a further embodiment, a piezo electric vibrator is applied at an optimum frequency and amplitude to accelerate ribonucleic acid adsorption onto the ribonucleic acid extraction and concentration chamber surface and subsequently with or without the use of eluent, release the adsorbed ribonucleic acid from the surface.

In a further embodiment, SYBR Green dye may be used with melt-curve analysis to distinguish the presence and amplification of double-stranded DNA (dsDNA) progressively constructed by repeated PCR cycles. Through this mechanism, the temperature at which the dsDNA melts (denatures into single strands) and thus distinguishes one molecular weight from another.

This summary is provided to introduce a selection of concepts in a simple manner that is further described in the detailed description of the disclosure. This summary is not intended to identify key or essential inventive concepts of the subject matter nor is it intended for determining the scope of the disclosure.

To further clarify advantages and features of the present disclosure, a more particular description of the disclosure will be rendered by reference to specific embodiments thereof, which is illustrated in the appended figures. It is to be appreciated that these figures depict only typical embodiments of the disclosure and are therefore not to be considered limiting of its scope. The disclosure will be described and explained with additional specificity and detail with the accompanying figures.

BRIEF DESCRIPTION OF THE FIGURES

The disclosure will be described and explained with additional specificity and detail with the accompanying figures in which.

Further, persons skilled in the art to which this disclosure belongs will appreciate that elements in the figures are illustrated for simplicity and may not have been necessarily drawn to scale. Furthermore, in terms of the construction, the microfluidic laboratory and one or more components of it may have been represented in the figures by conventional symbols, and the figures may show only those specific details that are pertinent to understanding the embodiments of the present disclosure so as not to obscure the figures with details that will be readily apparent to those of ordinary skill in the art having benefit of the description herein.

DETAILED DESCRIPTION

For the purpose of promoting an understanding of the principles of the disclosure, reference will now be made to the embodiment illustrated in the figures and specific language will be used to describe them. It will nevertheless be understood that no limitation of the scope of the disclosure is thereby intended. Such alterations and further modifications to the disclosure, and such further applications of the principles of the disclosure as described herein being contemplated as would normally occur to one skilled in the art to which the disclosure relates are deemed to be a part of this disclosure.

It will be understood by those skilled in the art that the foregoing general description and the following detailed description are exemplary and explanatory of the disclosure and are not intended to be restrictive thereof.

In the present disclosure, relational terms such as first and second, and the like, may be used to distinguish one entity from the other, without necessarily implying any actual relationship or order between such entities.

The terms "comprises", "comprising", or any other variations thereof, are intended to cover a non-exclusive inclusion, such that a process or method that comprises a list of steps does not include only those steps but may include other steps not expressly listed or inherent to such a process or a method. Similarly, one or more elements or structures or components preceded by "comprises . . . a" does not, without more constraints, preclude the existence of other elements, other structures, other components, additional devices, additional elements, additional structures, or additional components. Appearances of the phrase "in an embodiment", "in another embodiment" and similar language throughout this specification may, but do not necessarily, all refer to the same embodiment.

Unless otherwise defined, all technical and scientific terms used herein have the same meaning as commonly understood by one of ordinary skill in the art to which this disclosure belongs. The components, methods, and examples provided herein are illustrative only and not intended to be limiting.

Figure 6:
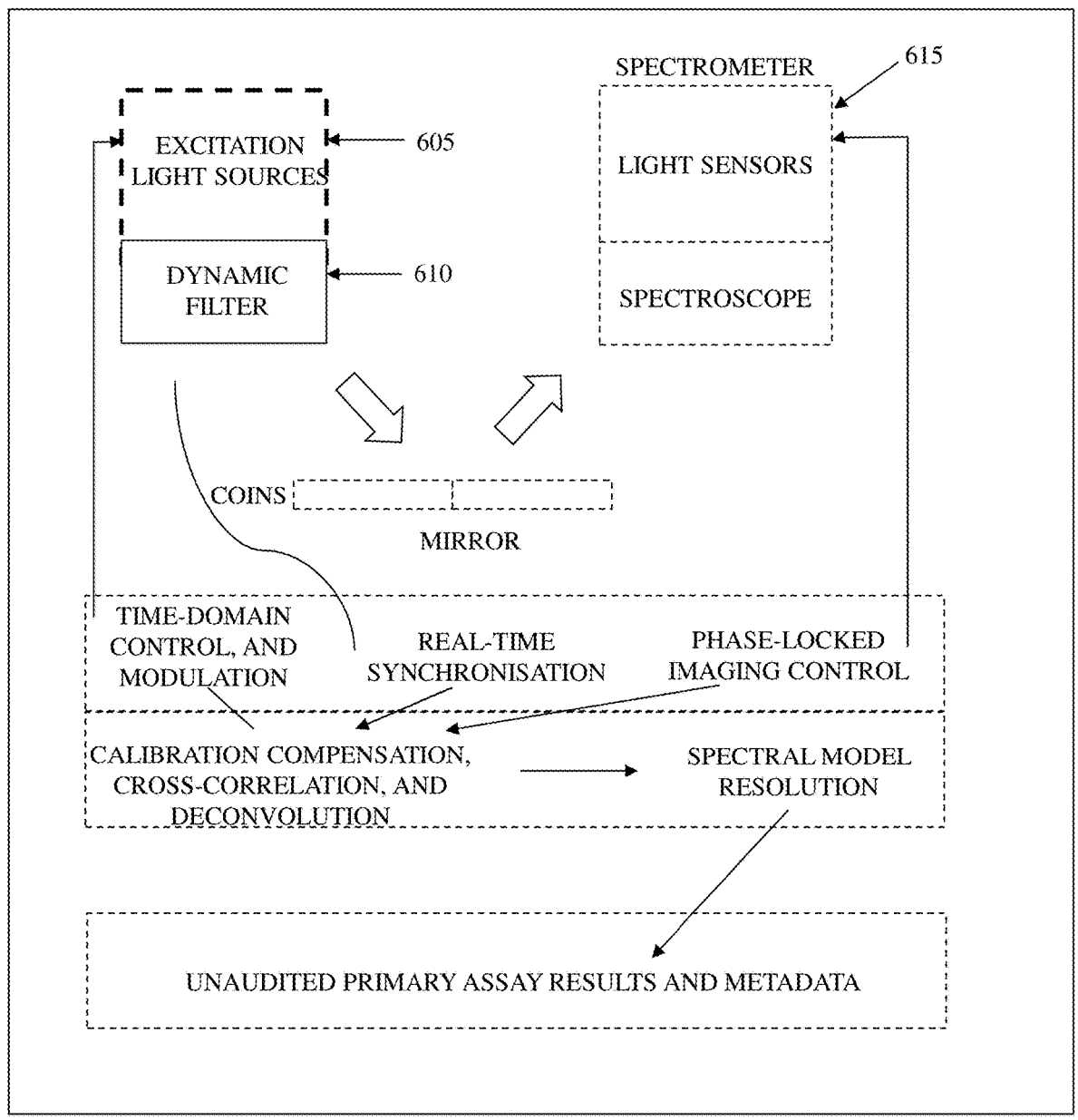
FIG. 6 illustrates block diagram of an optical process flow in the microfluidic platform, in accordance with one embodiment of the present disclosure.
Figure 7A:
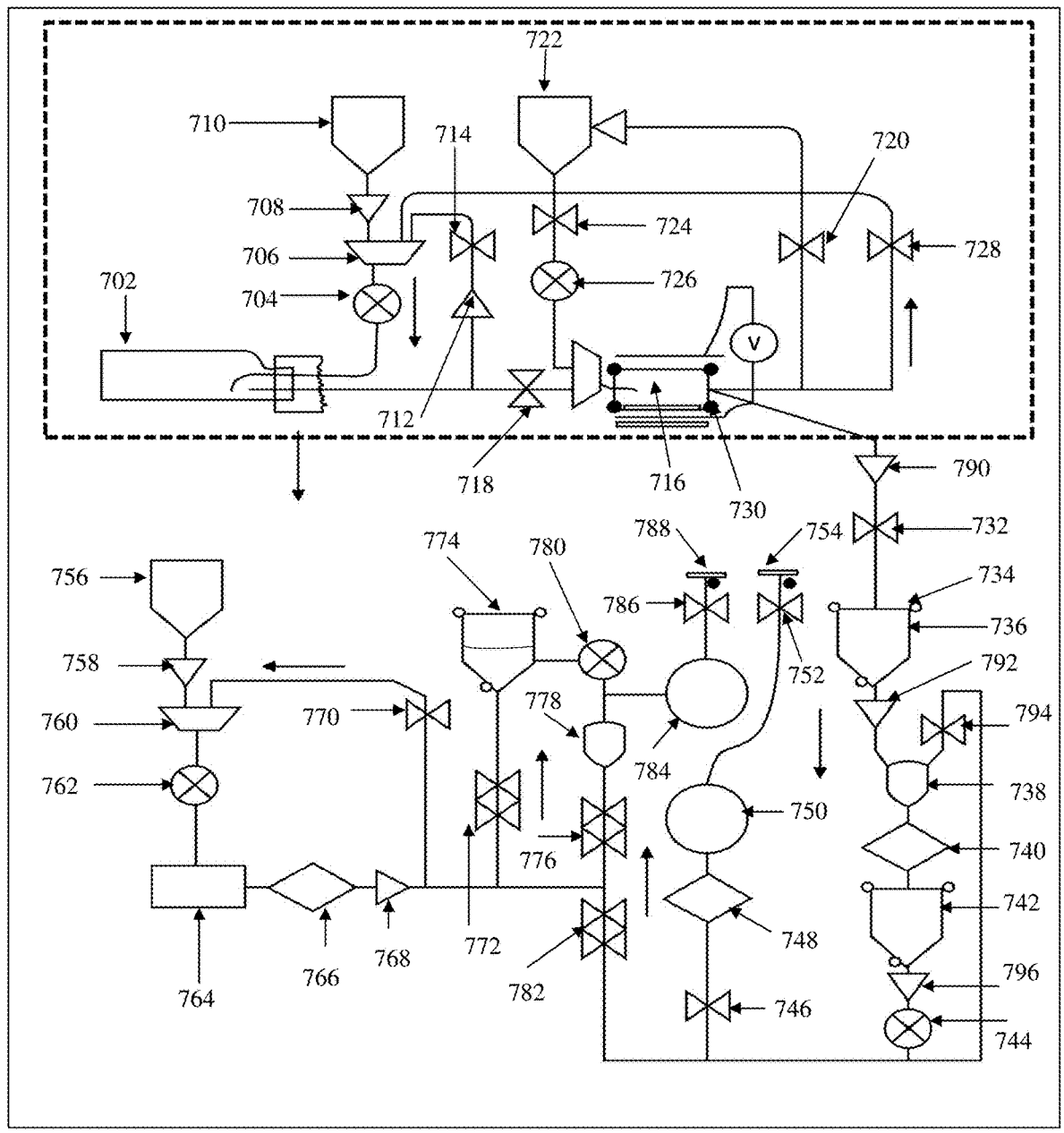
FIG. 7A illustrates complete flow sequencing in the microfluidic laboratory, in accordance with one embodiment of the present disclosure.
Figure 7B:
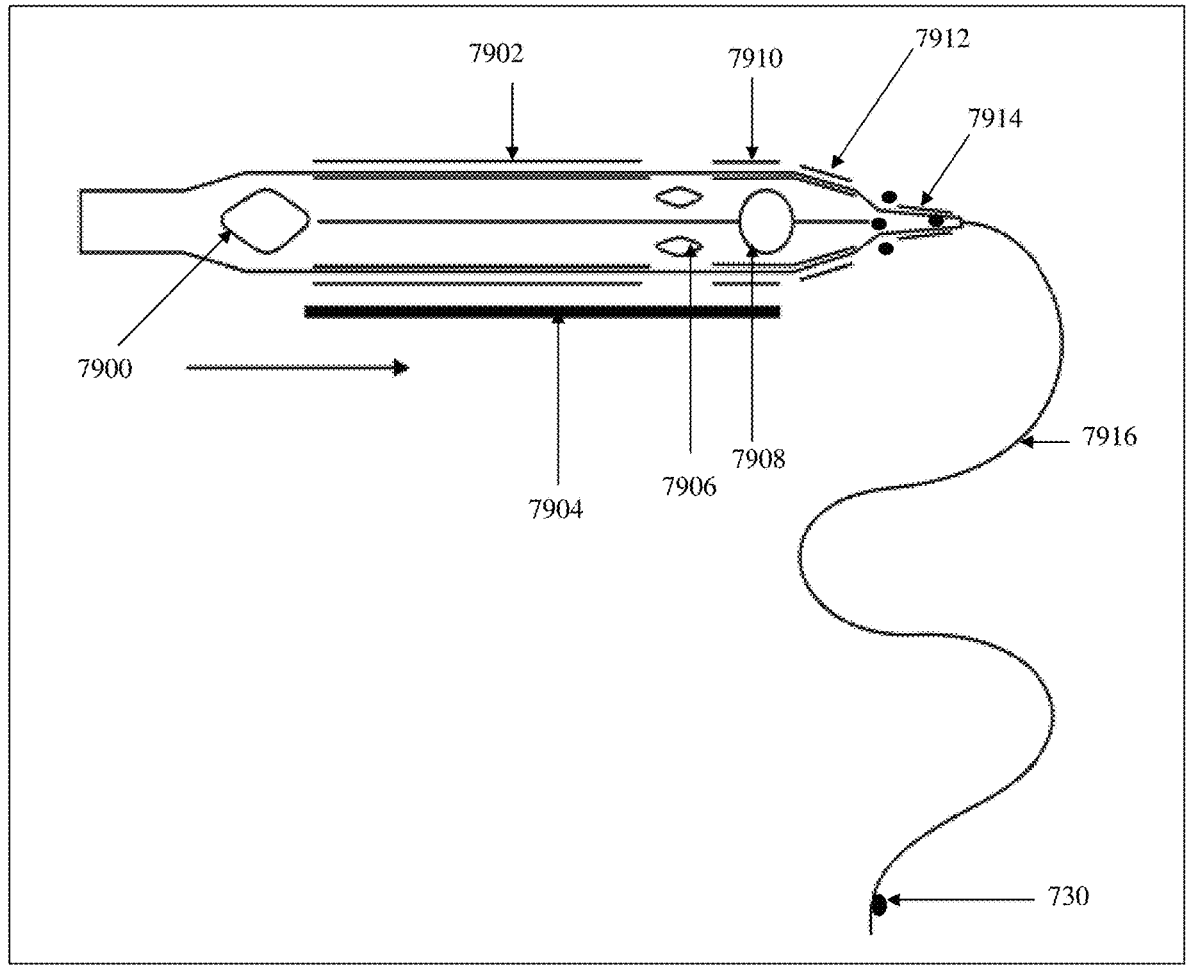
FIG. 7B illustrates an RNA extraction and concentration chamber in the microfluidic laboratory, in accordance with one embodiment of the present disclosure.

Embodiments of the present disclosure relates to a microfluidic platform and a method for reverse transcriptase quantitative polymerase chain reaction analysis. The microfluidic laboratory (MFL) is also called microlab and is interchangeably used in the remainder of this disclosure. The microfluidic platform represents the entire system and MFL is a part of the microfluidic platform. It is to be noted that FIGS. 1 to 6 illustrate the structural aspects of the microfluidic platform and the MFL, and FIGS. 7A to 7O illustrate the various sequence flows within the MFL.

Figure 1:
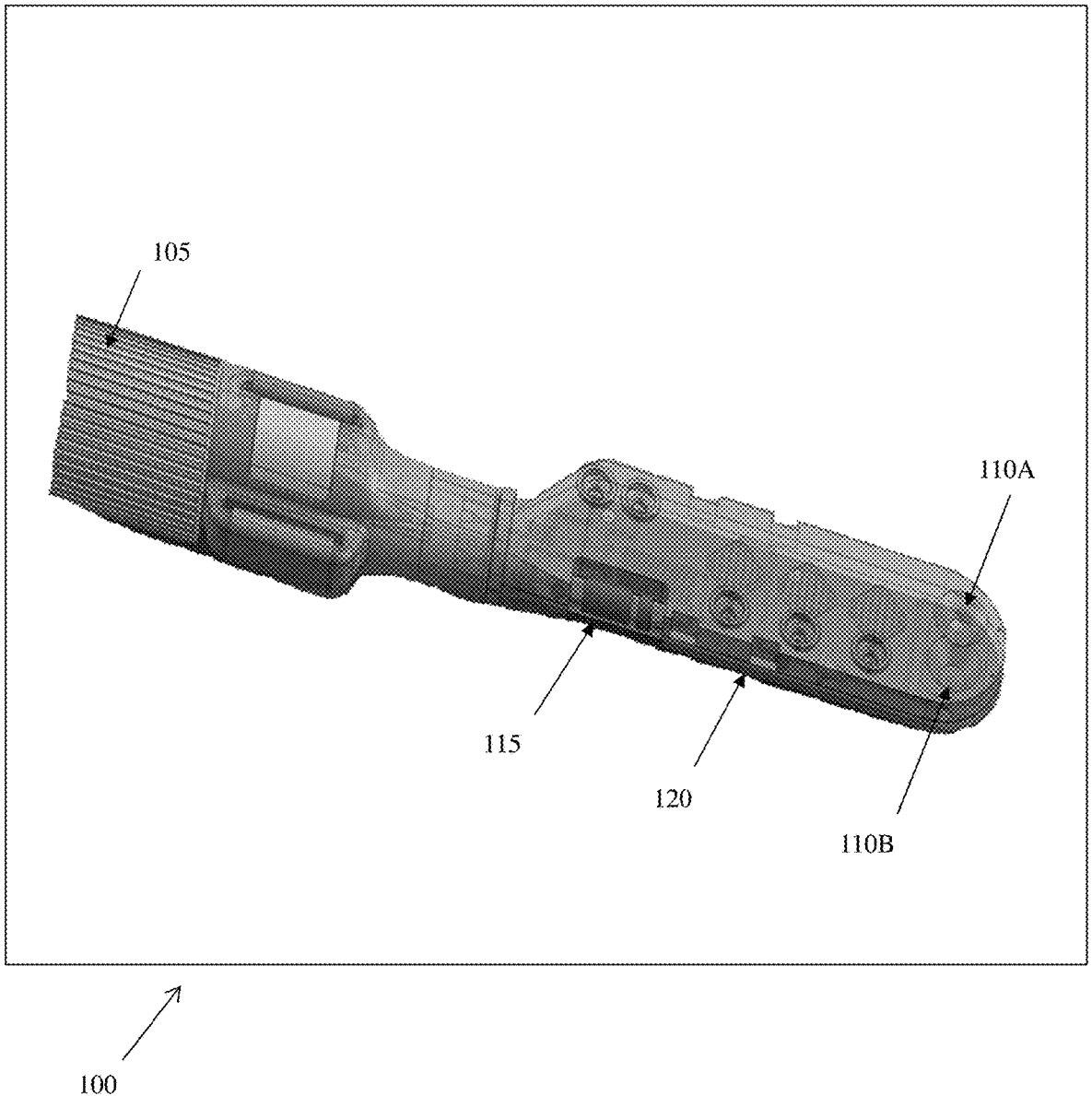
FIG. 1 is an illustration of a microfluidic platform for reverse transcription and quantitative polymerase chain reaction analysis, in accordance with an embodiment of the present disclosure.

Referring to FIG. 1, the figure is an illustration of a microfluidic platform 100 for reverse transcriptase quantitative polymerase chain reaction (RT-qPCR) analysis. The microfluidic platform 100 includes an integrated sampling tube 105, a microfluidic laboratory 120 that houses two coins (110A, 110B), an RNA extraction chamber 115, and other associated components, and optical subsystems and electronics (not shown in FIG. 1).

The MFL has two reaction cell coins ('coins'), one being an assay coin and the other a no-target control (NTC) coin. The coins include thermistors, a heat pump, a heat sink, a mirror, and a lens mechanism. Essentially, coins are reaction chambers where a master mix of various reagents, mix with the eluate having the extracted RNA. In one embodiment, to detect SARS-COVID2 virus, the master mix includes reverse transcriptase enzyme, taq polymerase enzyme, PCR primer, and a probe consisting of a dye that emits fluorescence when separated from a quencher molecule that otherwise prevents fluorescence. The mix of reagents can vary depending on the virus that is being analyzed and may also include a passive probe which fluoresces when illuminated by an excitation color irrespective of the presence or absence of the biological molecules sought by the assay. The mixing of the reagents with the eluate having RNA, causes reverse transcription of RNA into cDNA. Further, using qPCR, the coins provide amplification of specific DNA targets.

In a further embodiment, the use of PCR with reporter-quencher probes may be replaced by the use of SYBR green in an intercalating assay in order to differentiate multiple amplicons by melt-curve analysis. The methods discussed in the present disclosure is well suited to melt curve analysis as it handles each assay individually, assays with differing biological noise and contaminants. Unlike conventional primer-probe assays, SYBR green in melt curve analysis binds only to double stranded, dsDNA, not single stranded DNA and only fluoresces therefrom. Furthermore it does not independently fluoresce in solution. Consequently, when dsDNA is heated to its melting point and dissociates, fluorescence decreases. Different amplicons (where only one is expected to exist) will melt at different temperatures due to the difference in their molecular weights. Observing the sudden drop in fluorescence over temperature (the 'melt curve') allows identification of competing amplicons and by calibration, identifying each species.

The RoaaaR methodology of providing highly precise temperature control to individual assays facilitates mass deployment of melt curve analysis with co-processed and differing pathogens that is unavailable by standard, single protocol PCR machines.

The optical subsystems primarily include one or more light sensors for example CMOS or CCD linear arrays or area imagers, excitation sources for example light emitting diodes (LEDs), filters, and a mirror integrated to the coins. The mirror approximately doubles the amount of emission light from the assay reaction, equivalent to the system gain of a PCR thermal cycle. The photo detectors detect the emission from the coins. Successive images are captured and correspond to the emission spectra captured during sequential thermocycle iterations. It is another object of the present disclosure to reduce noise in the microfluidic platform. Noise reduction includes electrical, electronic, optical, and biological noise reduction. The microfluidic platform is designed to contribute to the reduction in the optical and biological noises and improve the signal to noise ratio. These noise reduction techniques work in concert with the other associated components of MFL include acoustic valves, acoustic pumps, multiplexers, reservoirs, reaction chambers, and sensors.

In one embodiment, the MFL in order to reduce the processing time and maintain high quality includes electrical sensors embedded in the MFL. The electrical sensors provide closed loop rather than less deterministic open loop fill periods for the various channels and chambers in the MFL. The conductivity sensors are connected to the controlling computer. They are used to detect when channels and chambers are full. They are also used to determine the real and complex electrical conductivity of the fluid in the respective channels and chambers in order to ensure these parameters are within intended limits and thus detect defective assays that might otherwise produce false negative or false positive results.

The microfluidic platform uses a RandOm-Access Analytical Array (RoaaaR) architecture to perform the reverse transcriptase quantitative polymerase chain reaction analysis. The MFL is pre-filled in the factory with reagents and then lyophilized (freeze dried). Performing the pre-filling step within a factory makes the MFL less susceptible to contamination, more consistent, and more accurate than conventional, laboratory-based qPCR techniques. Each patient sample is individually handled in a MFL and is introduced into an Analytic Cell (AC) as depicted in FIG. 2.

Figure 2:
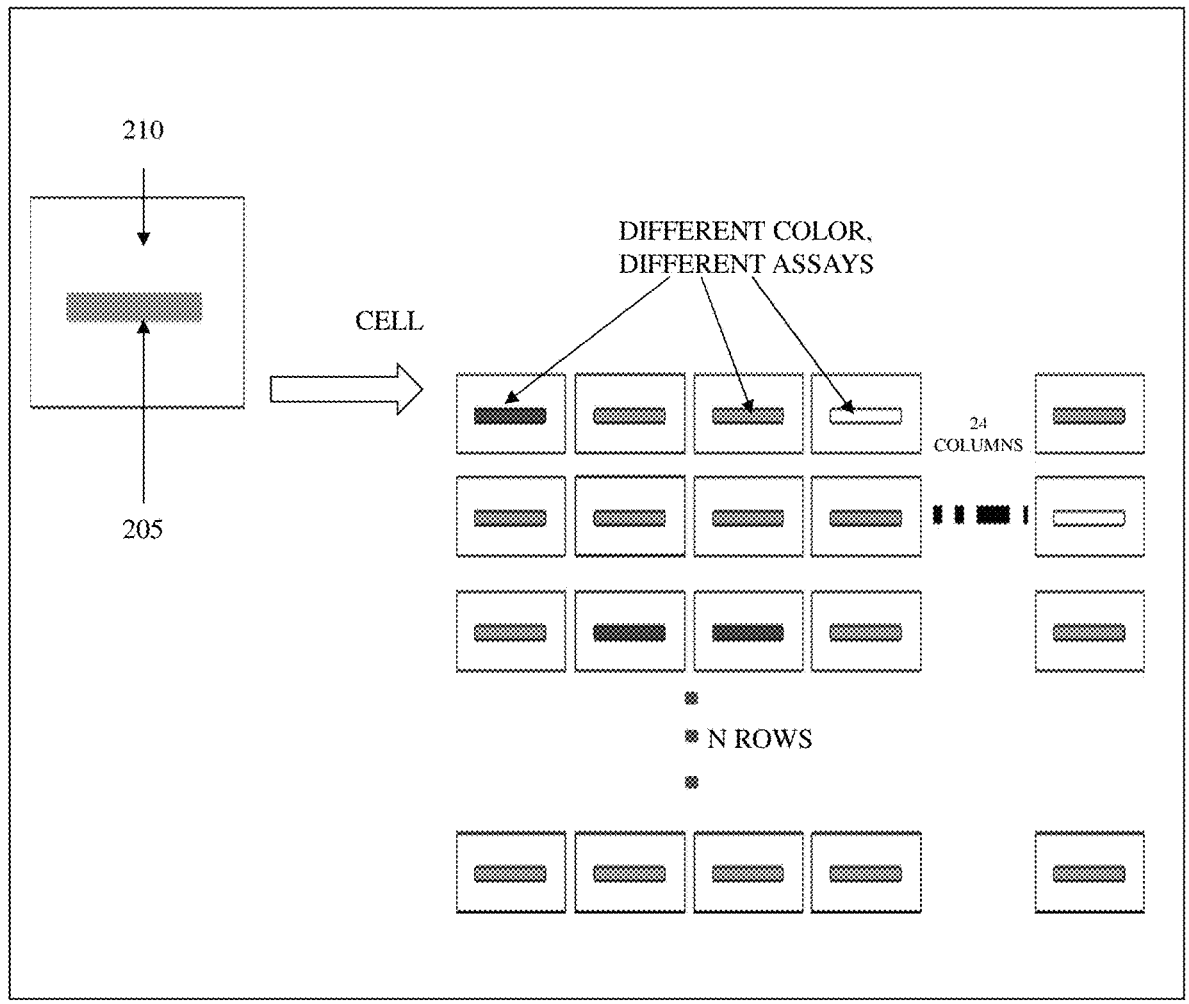
FIG. 2 illustrates a random access array, in accordance with an embodiment of the present disclosure.

The handling of the MFL and the various functions of the AC is further explained in conjunction with the description of FIG. 2.

Referring to FIG. 2, the figure illustrates a random-access array. Pre-processed samples from patients are first transferred into the sealed MFL 205 in a self-sealed environment. Each MFL 205 has a universally unique identifier (UUID) and is inserted into an AC 210 in the random-access array. Each AC 210 and the MFL 205 is calibrated during manufacture and provided with UUID. The MFL 205 is provided with an electrically erasable, programmable, read-only memory (EEPROM) to carry the UUID and test and calibration parameters and the AC 210 has stored UUID and test parameters in a Near-Field Communications (NFC) tag. This facilitates simple manufacturing and maintenance procedures with no requirement to breach packaging prior to installation. Optical marking such as bar codes or QR codes are used for optional stock control processes. NFC tags and EEPROM however facilitate data access even in the event of failure of Internet access.

In one embodiment, the random-access array includes 12 to 24 analytic cells per row, and up to 40 rows can be present. The quantity of rows is limited only by the height of the supporting machine chassis. MFLs are inserted manually or in high volume scenarios such as airports, the MFL 205 is inserted to the AC 210 by a loading robot. There is no use of micropipettes, syringes or similar mechanisms nor is there a risk of aerosol contamination. Each AC 210 operates autonomously, executing the assay protocol for the sample and target pathogen contained in the MFL 205. In one embodiment, the AC 210 includes a microlab receptacle, a connector circuit board to mate with the microlab integral circuit board, a Peltier heat pump, an optical sub-system, front panel status indicator lamps, and an analysis cell controller. The analysis cell controller reads calibration data from each microlab as presented. Further it loads the chemistry and temperature profile from the microlab. The analysis cell controller reads stored calibration data, controls the heat pump gain, thermal mass, power saturation limit and runs a thermocycler. Further, analysis cell controller, measures the resistance of each No-Target Control (NTC) thermistor(s), corrected by the calibration data. The analysis cell controller calculates the current temperature, runs the heat pump closed loop control according to the next temperature required in the cycle protocol, detects saturation conditions, detects open loop gain not matching recorded level and informs the Instrument State Sequencer (ISS) the state of a given AC both on demand and autonomously, if it needs to take action in the event of a defect. The analysis cell controller monitors for several alarm conditions detected via the MFL, passing the alarm event to the ISS, reports the cell's position to the ISS, informs the Array Metrology Module (AMM) when optical analysis is needed, and informs the ISS when a microlab is ready for removal. In the event the microlabs are picked up and placed in the AC 210 by the handling robot, the robot places the microlabs located into a vacant AC position. During microlab transfer, the QR code is read. After insertion into the array, the UUID of the microlab is reconciled with the EEPROM stored version.

Figure 3:
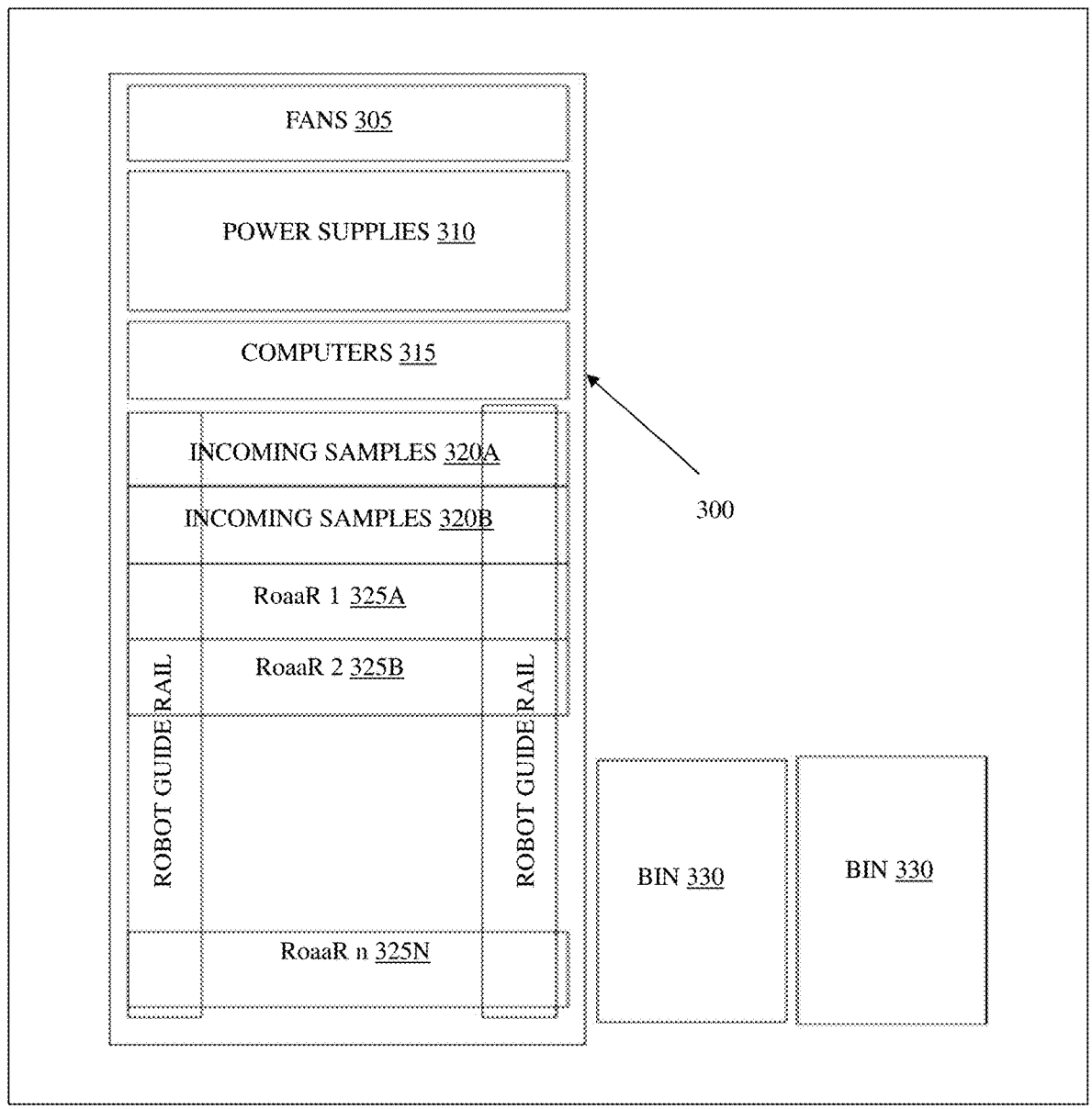
FIG. 3 illustrates a 19" rack unit, in accordance with an embodiment of the present disclosure.

FIG. 3 illustrates a 19" rack unit. In one embodiment, the random-access array having the analytical cells is mounted on a 19" rack unit 300. The 19" rack unit 300 is a widely available standard rack in data management centers that comes with widely available, frame structure, door, racking, ventilation, power supplies, cable management, and ancillary parts. In one embodiment, the 19" rack unit 300 includes a fan 305, power supplies 310, computers 315, incoming samples (320A, 320B . . . 320N), RoaaaR architecture implemented microfluidic platforms (325A, 325B . . . 325N), robotic guide rail, and bins 330. The power supplies 310 are designed to mitigate any risk of power failures. For example, a power supply unit can be split into four banks that will provide a power supply of 2 kW/bank. In the event of failure, each hot-swappable bank shall be fully isolated from the others. The fan 305 provides the necessary air cooling and is designed for fan failure detection and shutdown mitigation. Most of the power is consumed by the thermoelectric heat pumps. Typically, these consume 8 W at full cooling for the size of Peltier pumps in the rack. Of that, about 25% is available to cool the coin of each analytical cell. The liquid volume of each Coin, at approximately 300 nanoliters, is negligible. Taking the coin volume as 1.44 mm3, and the material as acrylic, with a density of 1190 kg/m3, the coin has a mass of ~1.8 mg and therefore a heat capacity of 0.003 J ° C. Hence over the 30° C. to 95° C. interval used in a typical thermocycle of a qPCR system, 0.16 J must be transferred which will require approximately 20 ms per cycle transition for heating/cooling time. In contrast, the water in the coin requires less time for the same transition at the same input power. In practice parasite loads such as the surrounding plastic and the Peltier heat pump itself will dominate the power consumption. Therefore, minimizing the coin mass is pivotal to high speed operation, as is the available power through the heat pump.

Figure 4A:
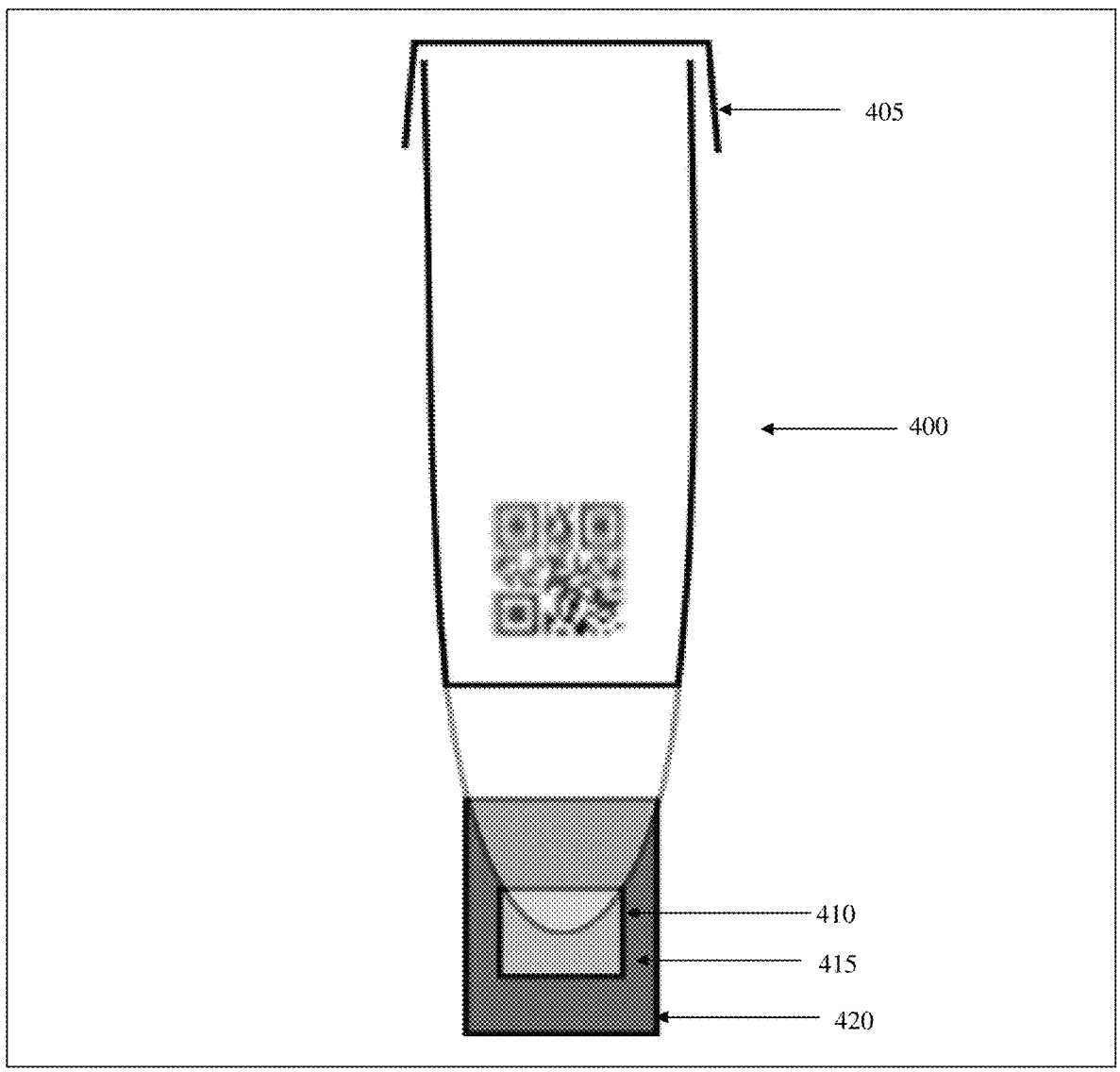
FIG. 4A illustrates a sampling tube, in accordance with one embodiment of the present disclosure.
Figure 4B:
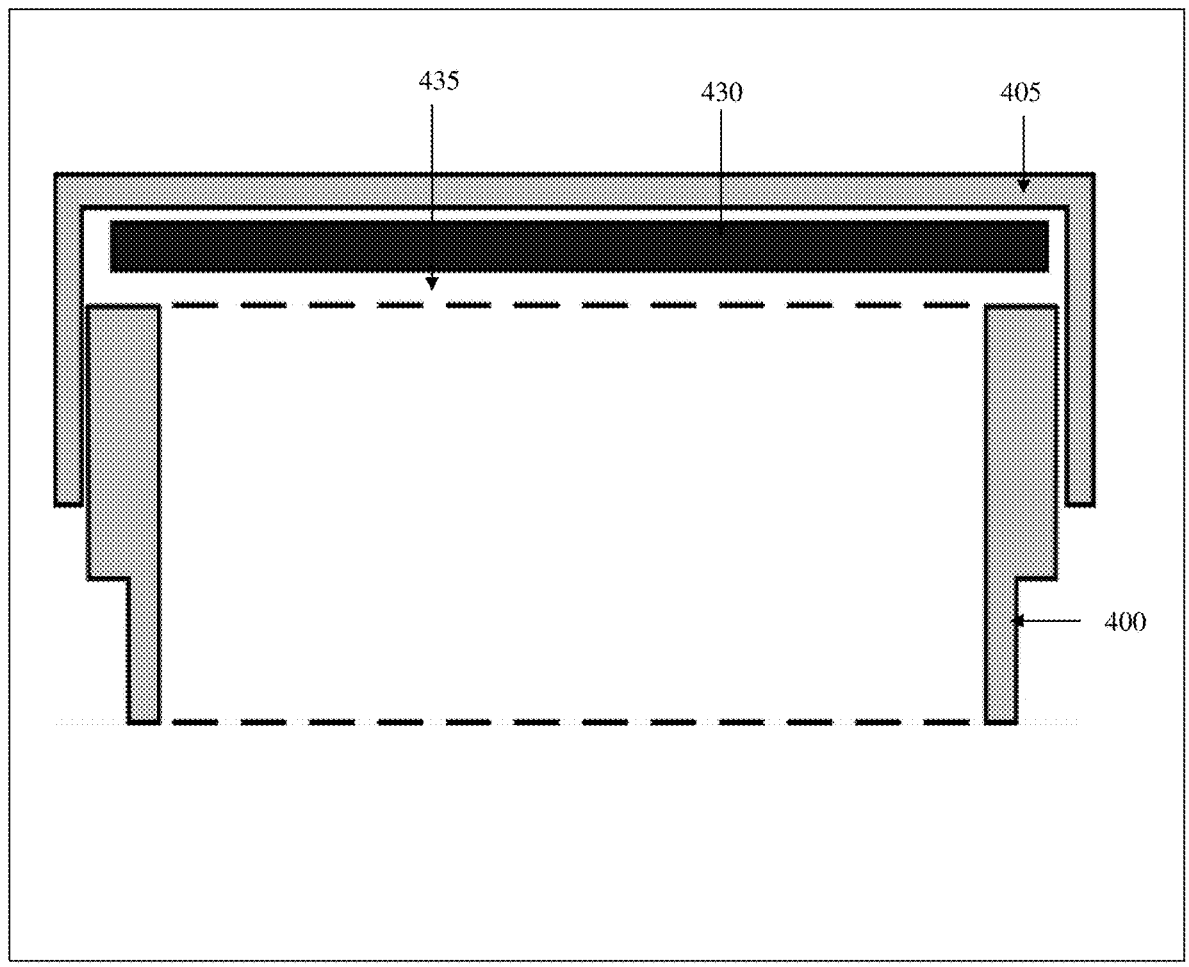
FIG. 4B illustrates a cap portion of the sampling tube, in accordance with one embodiment of the present disclosure.

FIG. 4A illustrates a sampling tube 400. In one embodiment, a sampling tube is used separately to collect the saliva sample and can be coupled to the MFL for analysis. In another embodiment, sampling tube is integrated with the MFL as a single unit. Described below is the embodiment wherein the sampling tube is separate from the MFL. The tube 400 has a special cap 405 to ensure it is fully airtight and watertight. The tube 400 is confirmed closed by manual inspection, and by visual and audible indications. The act of closure is unidirectional, and the cap 405 cannot be undone other than by destruction. The cap 405 is secured with a steep but fine pitch. Either a compression or a rotation action will close the cap 405 onto the tube 400. The thread or threads have many fine barbs which provide a ratchet action. When compressed or rotated far enough, a pre-loaded plastic spring, actuated by the closure action, pulls the cap 405 into full engagement with the tube 400, locking the two parts together and giving an audible indication. In another embodiment, the spring also moves a visible flag, so there is optical indication of closure. A lens molded into the outer surface of the cap allows an external opto-electronic sensor to detect operation of the closure and sealing mechanism. No conventional adhesives or elastomer foam of any sort need to be used to seal the mating surfaces of the tube 400 and cap 405. Instead, the upper inside surface of the cap has concentric rings of polythene which mate with shallow negative profiles on the outer sloping rim of the tube 400. The compression of the rings prevents egress of the contents in the tube 400. The closure of the tube 400 may be inspected by using an RFID or an optical test pattern. The tube 400 with the RFID tag 430 is illustrated in FIG. 4B. The gap 435 will be closed when tube 400 and the cap 405 are properly mated.

Liquid lysis buffer or any other preparatory sample treatment may be stored in a compartment in the sampling tube 400. Within the embodiment of a separate sampling tube and MFL, the tube 400 includes a sealable port 410 enclosed in a port cover 420 having a clean cavity 415. The port 410 is designed to have a rupture mechanism that only releases the one or more reagents when the sampling tube is mated with the MFL. Once mated with the MFL, the fluid containing the sample, preservative (if used) and lysis buffer is transferred to the MFL via the port 410. After transfer, the tube 400 and MFL remain mated to avoid the risk of inward contamination of the MFL, or the leakage of hazardous material. After mating, powerful UV lighting can be used to clean the outside of the tube 400. In the embodiment with an integrated sampling tube and MFL, the sampling tube 400 and the MFL are internally connected with fluid and gas interchange channels and no sealable port is required.

Figure 4C:
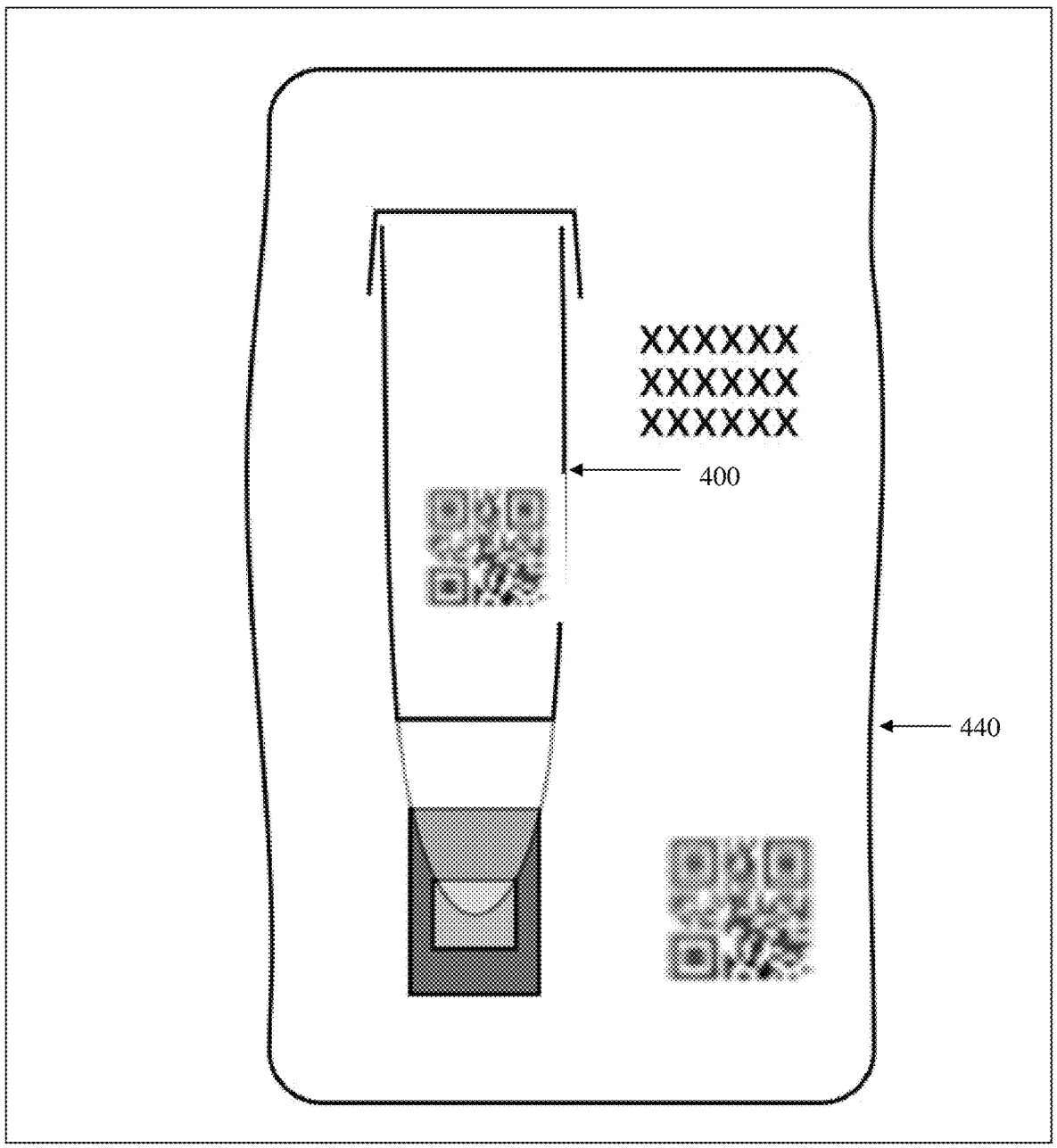
FIG. 4C illustrates the sampling tube disposed in an envelope, in accordance with one embodiment of the present disclosure.

The tube 400 may be enclosed in an envelope 440 as depicted in FIG. 4C. Cleansing of the envelope inner and outer surfaces and of the tube outer surface is conducted with high-intensity UV-C light. This is done to remove any biologically active contaminants that may be on any exposed surfaces. The use of a UV-C opaque material for the sampling tube and MFL either in the separate or integrated embodiments whilst manufacturing the cap with a UV-C transparent outer collar allows pathogens trapped on the surface between the sampling tube and the cap to be destroyed.

Figure 5A:
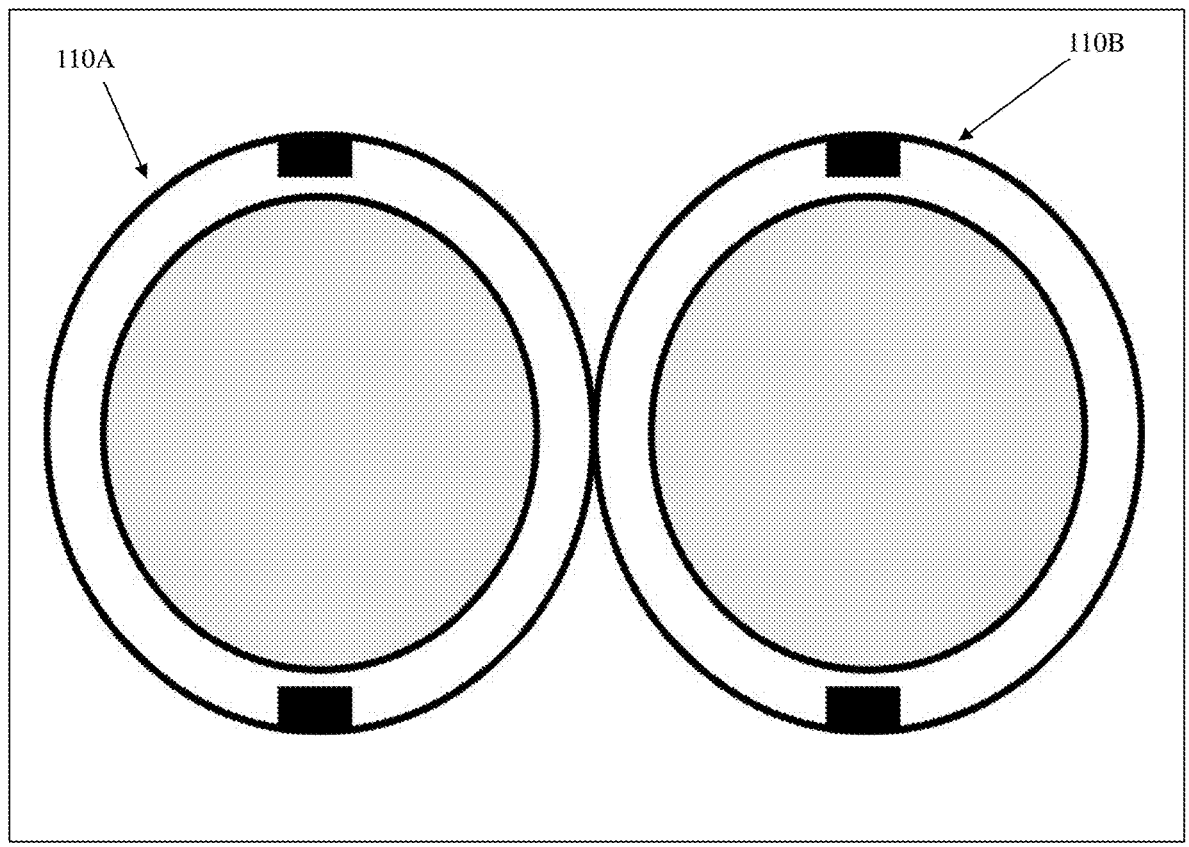
FIG. 5A illustrates a plurality of coins in a microfluidic laboratory, in accordance with one embodiment of the present disclosure.
Figure 5D:
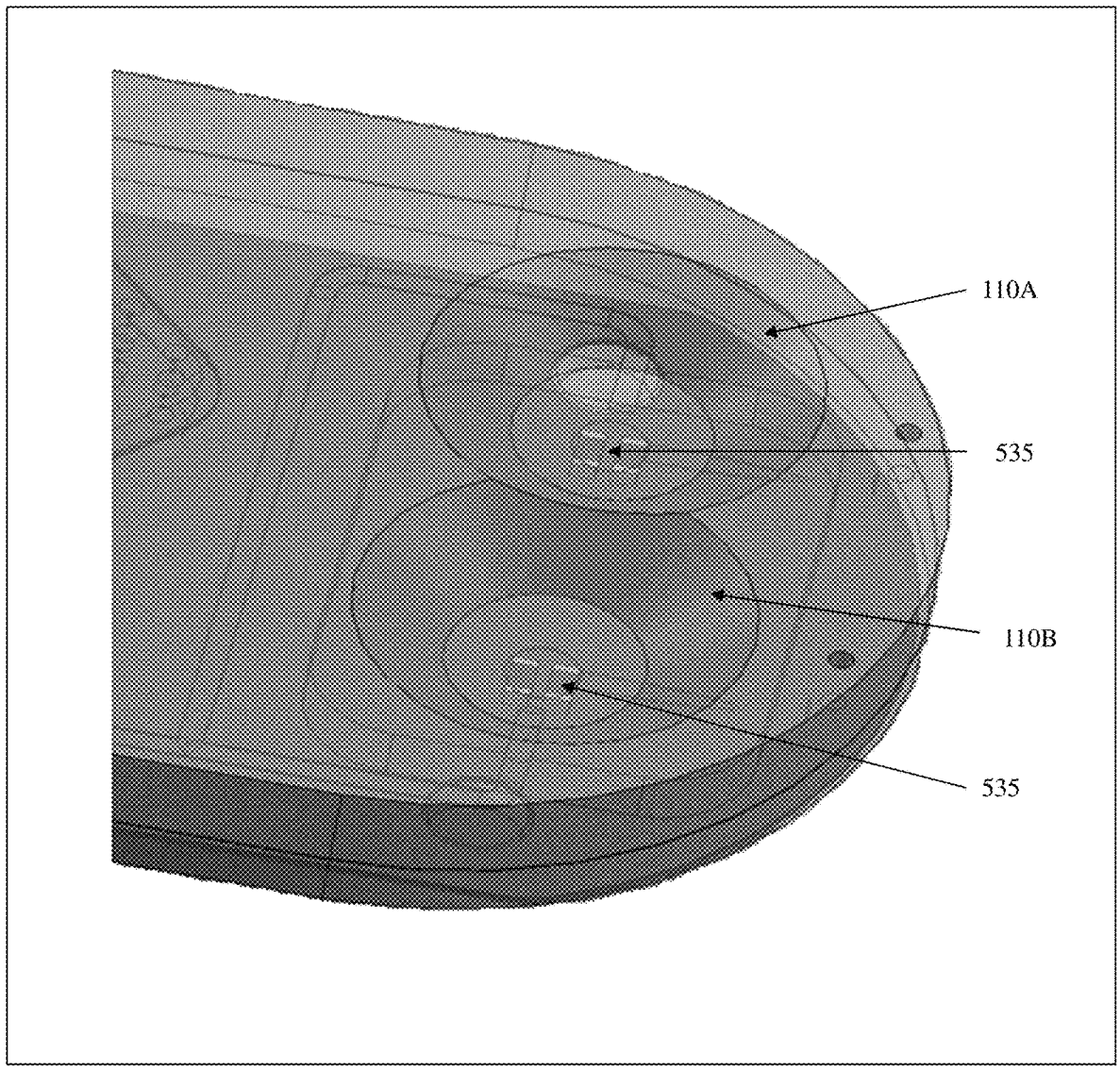
FIG. 5D is an illustration of the placement of the reaction cell coins in the microfluidic laboratory, in accordance with one embodiment of the present disclosure.

FIG. 5A illustrates coins in a microfluidic lab. There are two coins in the MFL. One coin is the assay coin 110A and the other coin is the no-target control coin 110B. Essentially, coins are reaction chambers where a master mix of various reagents mix with extracted RNA. In one embodiment, the coin(s) are placed on far right of the MFL as depicted in FIG. 5D.

Figure 5B:
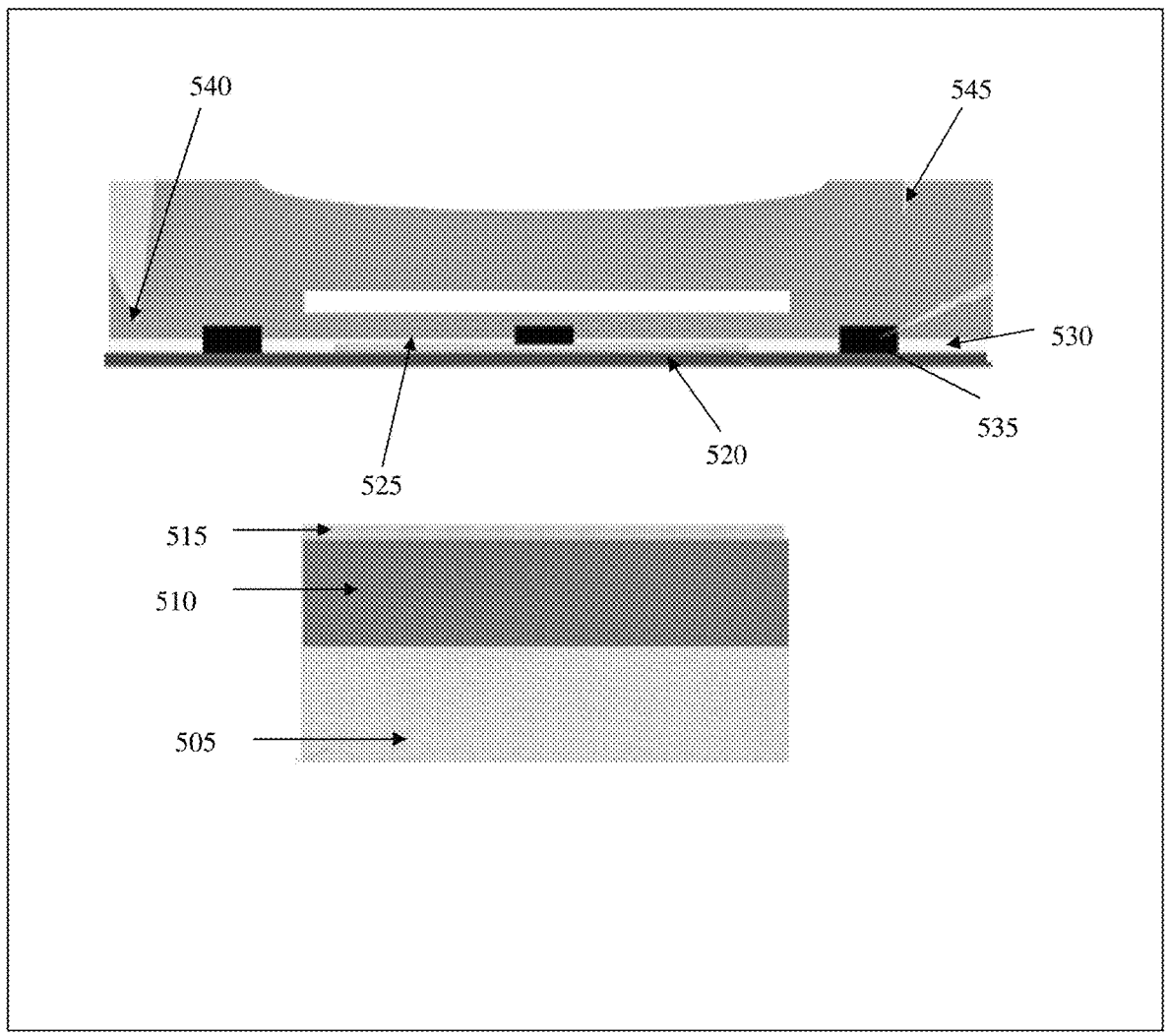
FIG. 5B illustrates basic elements of a reaction cell coin in a microfluidic laboratory, in accordance with one embodiment of the present disclosure.

The basic elements of a coin 500 are depicted in FIG. 5B. The coin includes a heat pump 510, heat sink 505, and a thermal gasket 515. The coin 500 is integrated to a printed circuit board (PCB) 520, a piezo mixer 525, a mirror 530, and thermistors 535. The coin 500 includes a lower molding with a cavity 540 and an upper molding with integrated lens 545. Each Coin is surrounded by two, low cost NTC thermistors, yielding four thermistors from which to take temperature measurements during an assay process. The MFL including the coins are calibrated in production, with the curve parameters stored both in the cloud and in non-volatile memory of the PCB 520. The requirement to support two analysis regions provides the requirement to adopt two chambers in the coin. In one embodiment, each of the two-coin chambers can hold a volume of 300 nl.

During operation, the thermal gasket 515 of the heat pump 510 is in contact with the underside of the PCB 520. Both Peltier heat control and piezo mixing must apply to both coins to ensure uniformity of reaction conditions. Pivotal to the PCB's role in the thermal cycling is that with the embodiment not using a piezo mixing element the thermoelectric heat pump—a Peltier effect element—offers up its contact face to the rear of the PCB 520. In the embodiment using a piezo mixing element, the upper face of the PCB 520 underneath the coins is equipped with the piezo mixer 525. This places the PCB 520 between the heat pump 510 and the coins, thereby reducing thermal conductivity. The closed loop control 550 adjusts Peltier effect element's power input to match the desired rate of change of temperature at the NTC thermistors. The piezo provides acoustic steering of the liquids by sending acoustic waves through the material.

The mirror 530 is deposited on the underside of the coin(s). The mirror 530 reflects fluorescence emitted toward the underside, back upwards, through the medium towards the light sensor as depicted in FIG. 6. For optimum performance the mirror should be plated to the underside of the coin. In one embodiment, the mirror 530 is plated onto the piezo vibrator 525. The mirror 530 provides maximum photon flux, by capturing light that would otherwise be lost to the surrounding environment. This has the approximate effect of reducing the cycle count for a positive diagnosis by a single PCR cycle. To give an example, when used at scale, the efficiency improvement by the mirror 530 is approximately a 3% improvement in facility throughput i.e. 3,000 samples a day for a 100,000 sample facility. In addition to reducing the cycle count, the mirror 530 enables detection of fluorescence, and thus of disease, at a reduced count of fluorophores, which in turn reduces the Limit of Detection (LoD) for the system.

The mirror 530 is also used for reverse transcription loop-mediated isothermal amplification (RT-LAMP, or simply LAMP) chemistry within the MFL. LAMP uses passive light transmission as the diagnostic indicator. The mirror 530 is particularly well suited to LAMP use, as the light must pass through the medium twice. LAMP's strength lies in its use as a direct, human-readable result. Mass, high volume testing cannot realistically exploit human readability due to the bottleneck this represents in noting the result and recording it. In the context of this disclosure wherein temperature transitions are very rapid, being negligibly short in duration compared to reaction times, the use of a static temperature has little beneficial impact compared to PCR temperature cycling. However, the microfluidic platform works equally well for LAMP as for PCR. Within the context of this disclosure and in any embodiment, where LAMP is the required chemistry, the advanced optical detection system of this disclosure in conjunction with the mirror will yield faster and more accurate results due to the highly sensitive and accurate colour detection. Is strongly beneficial within the embodiment of a personal, hand-held microfluidic platform analyzer using the RoaaaR architecture or portable microfluidic RT-qPCR analyzers in the same context. For all these embodiments, the coin 500 includes an upper molding with integrated lens 545. The lens 545 optimizes the effective aperture available in the optical sub-system.

Since RoaaaR architecture emphasizes area over sample volume in each micro laboratory, material volumes are very small. The optical subsystem is designed to detect the simultaneous presence of multiple probe dyes. This use of multiple dyes and therefore of emission wavelengths is known as 'multiplex' chemistry. It is therefore necessary to simultaneously analyze multiple wavelengths effectively in multiple coins across multiple assays being executed at the same time. To substantially reduce the cost of processing compared to prior art solutions sample analysis and controls are divided into three domains:
1. Wavelength multiplexing to analyze several reactions in the same volume of material.
2. Spatial multiplexing akin to conventional 96-well trays, but only having two 'wells', i.e. the two coins.
3. Temporal multiplexing, where some of the control reactions are undertaken at a different time to others.

The disclosure exploits the system characteristic that each sample presented to the machine will be presented before the sample presented immediately afterwards. Each sample begins execution of its assay process immediately it is accepted into the machine. This asynchronism between individual tests allows the overall system to undertake optical inspection of one test in the time other do not need it. Then, as the recently-inspect tested continues to its next phase, some other test is optically inspected. In this manner, the optical inspected components of the system are shared between multiple tests, keeping the optical subsystem in continuous use. In one embodiment this multiplexing is achieved by switching the excitation LEDs of a given test on or off so as to only excite one test at a time and hence only obtain the emissions of one test at a time. Further details are provided below.

The optical subsystems further include a diffraction grating which produces a spectrum from the incoming light sources and a 2D CMOS imager which allows for simultaneous spectral analysis of both coins: the donated sample and the No-Target Control. The RoaaaR architecture allows modulation of the excitation light source, which is used to facilitate temporal multiplexing and crucially, electronic, and biological noise reduction. The microfluidic platform having the RoaaaR architecture further performs Exciter-Modulated Fluorophore Correlation (EMFC). EMFC exploits the requirement of PCR reporter dyes to be illuminated in one color in order they fluoresce in another. With no excitation, there is no fluorescence. This exploitation allows to remove any background light from the analysis by subtracting any signal obtained when there is no excitation or a different excitation. Historically, this has been a limiting factor in reducing the process time of qPCR. It is usually necessary to execute sufficient thermal cycles for the chain reaction to produce a distinctive signature, separable from the background and biological noise. 'False' targets will also produce a different sigmoid curve growth response, further assisting the signal-to-noise enhancement. It is expected that this reduction in the signal to noise ratio will enable the microfluidic platform to detect the distinctive signature of a geometrically growing Covid pattern in about half the number of cycles needed. This reduced cycle count will accelerate the process of test analysis and produce test results faster. Using the RoaaaR architecture based microfluidic platform, an output reaching 2,000 to 60,000 tests per day can be achieved.

The RoaaaR architecture allows multiplexing of the optical detector between multiple Analytic Cells. With no excitation, the spectrum of all low level, constant sources can be assessed. This signal can be subtracted from the signal obtained illuminating each AC served by a given optical subsystem. Thus, by selectively activating the excitation of each AC, RoaaR architecture allows analysis of a single desired MFL, without affecting any other MFLs in the system. Modulation of the exciter wavelength allows to better distinguish between the desired signal and unwanted emissions close to the desired one. This is because the fluorescent emissions are not monochromatic, they usually span a significant portion of the spectrum, and these portions can overlap. Cross-correlation of the emissions with a theoretical model of the expected emissions with the actual signal allows demultiplex the several intended and expected signals from the various reporter dyes in the oligonucleotides more accurately. The RoaaaR architecture allows to better distinguish the emissions level before and after the reporter dyes are separated from the quenchers. The widespread use of passive dye serves to normalize all other measurements to an absolute value. One of the historical vulnerabilities of passive control is bubble formation in the sample medium. The active assay if carrying the target pathogen, will follow a sigmoid curve, and any trapped air will only reduce the absolute emissions. An area:depth ratio of 10:1 or greater is used that enables bubble removal in the MFL.

The microfluidic platform allows fine and accurate temperature control. Biological noise is reduced by consistent and accurate temperature control of the reaction chamber. It is necessary to be able to record the temperature throughout the processing period for either PCR or LAMP so that the temperature is within bounds specified. Low-cost temperature sensors such as NTC thermistors 535 generally have a tolerance of 5% for each of their characteristics. Greater precision such as 2% is readily available at slightly greater cost. The characteristics of each microfluidic platform once measured though are relatively stable if self-heating is avoided. For this criterion, the power dissipated through a device during operational measurement must be <=0.1% of the amount necessary to raise its temperature by 1K. It is intended 0402-sized components are used. Intrinsically being of small volume and mass, these are more sensitive to self-heating. Calibration is undertaken at 1 mA, with a 1% duty cycle. Operationally, the pulse width modulation of the operating current imposes a requirement for the modulation frequency to be at least 100× the closed loop frequency of the temperature control loop. The calibrations must be done at the same frequency.

In one embodiment each coin is surrounded by two, low cost NTC thermistors, with four in each MFL. These are calibrated in production, with the curve parameters stored both in the cloud and in non-volatile memory in the microlab's circuit board. During operation, the qPCR thermocycler uses the calibration information to compensate the measured sensor values to resolve the temperature accurate to at least 0.1° C. This temperature accuracy of +/−0.1° C. is about 2.5× more than existing qPCR systems available. The use of four thermistors, two for each Coin helps ensure the reaction chamber is equally heated and cooled and there are no significant hot or cold spots. It will help expose thermistors that have been damaged prior to use. The temperature uniformity across the Coin is 0.05° C. and is about 10× more uniform than existing qPCR systems available. Data from the thermistors is used in closed loop control of the heating and cooling of the Coin. The primary active element is the Peltier heat pump 510, which is provided with an individual closed loop control 550, per test site (i.e. per microlab position) as described below.

Figure 5C:
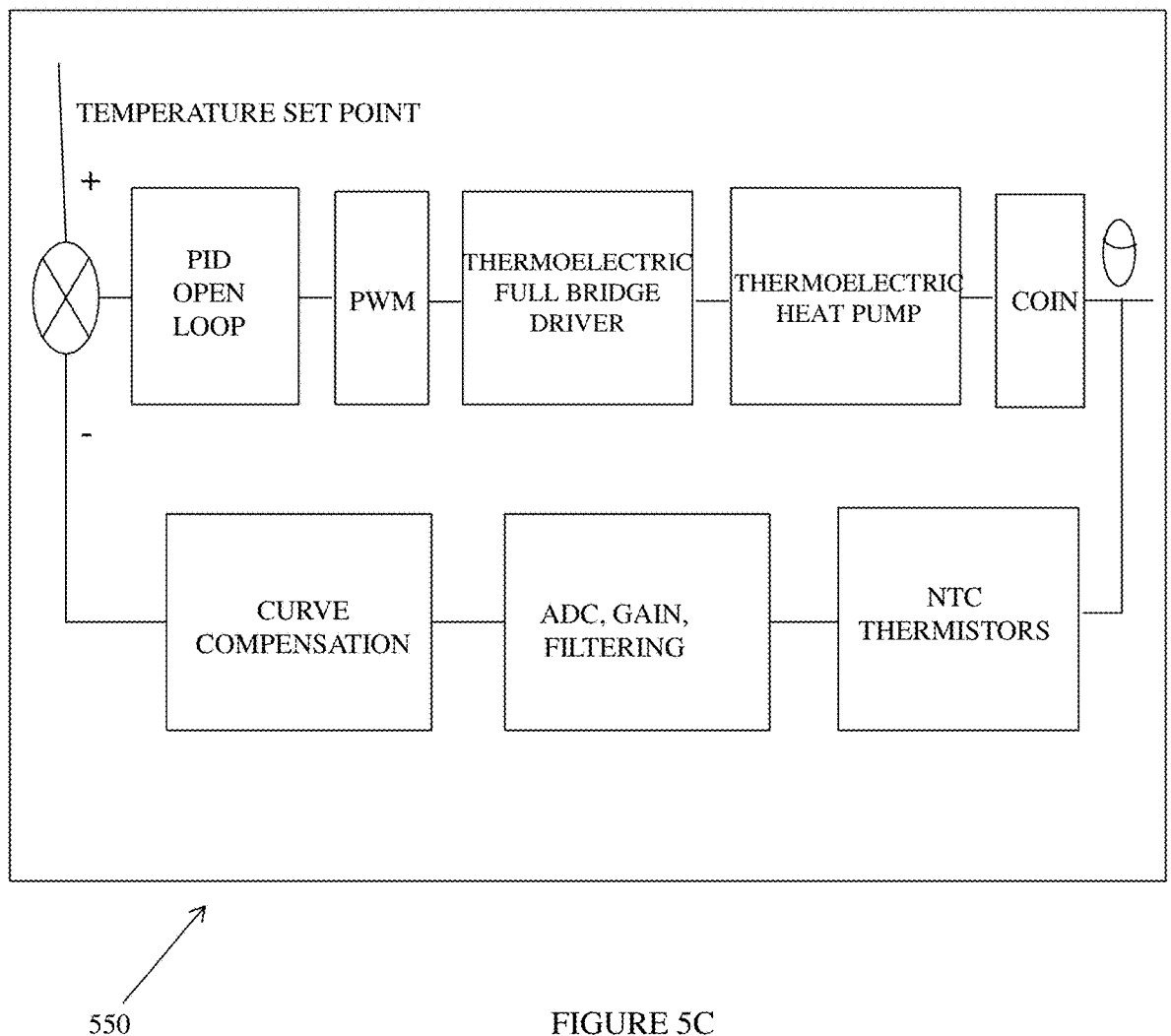
FIG. 5C illustrates a closed control loop of a coin, in accordance with one embodiment of the present disclosure.

Referring to FIG. 5C, the figure illustrates a closed control loop 550 of a coin. The heating and cooling of the coin is controlled through a closed loop control. Typically, PCR thermal cycling spans ~30° C. to +98° C. The upper temperature range is for the purpose of denaturing the cDNA. The reaction mix must not be allowed to boil. With a vented MFL, this puts an upper limit on the operating altitude. Unvented microlabs can exceed the limit imposed by the altitude. The limit will depend on the reagents in use. Typically, they will impose an altitude limit of between 2000 m and 5000 m. For example, in the USA, chemistry operable at 5000 m includes all settlements with a permanent population. However, vented designs may only be processed in a central laboratory setting due to the risk of pathogen release. This requires an ancillary design and a specific reference in the microlab non-volatile data storage. In the case of unvented embodiment, the closed environment will permit some small increase of permissible altitude although the chemistry will require re-calibration for non-standard air pressure. Below 2000 m the entire temperature span exceeds room temperature. That will not universally be the case, especially in rural tropical locations. In these cases, the Peltier effect heat pump will provide cooling below ambient to reach the primer annealing temperature. Otherwise heating is required, and active cooling only plays a role when reducing from cDNA denaturing down to annealing. An ancillary resistive element is included for heating. This may be used to assist or replace heating with the heat pump 510 as it has a much lower mass. Each heat pump 510 are backed by a heatsink 505 with forced air cooling to ambient. The heat sink 505 acts as an infinite heat sink and therefore the reference for the heat pumps connected to it. This sets the temperature gradient across the heat pump 510. In a further embodiment, a resistive heater may be applied at the same time as the thermoelectric heat pump in heating the coin. The heating element is a printed circuit pattern inside the microlab PCB. The PCB is only rated for five complete, 40-cycle runs, meaning it is possible to reuse the PCB five times before it must be recycled. The thermoelectric heat pump is under PWM control with a full bridge driver to eliminate a dead band between heating and cooling. The PID loop is nominal, selected because of the ease of specifying the loop characteristics by way of coefficients.

FIG. 6 illustrates optical process flow in the microfluidic platform. Excitation light sources 605, for example, Light emitting diode (LED) provide the necessary light excitation to the MFL. It is possible to modulate the light source in real time. Further, it is possible to perform real-time synchronization of the dynamic filters. Dynamic filter 610 provides a series of images with temporal offsets to the filter wavelengths. This is used to provide a more comprehensive excitation model. Multiple images with offset, sequential passbands allow for accurate modelling of ideal filters with non-ideal hardware. The light sources split into a spectrum and further is narrowed and focused onto the coins in either of the following embodiments: direct illumination for small, 'personal' systems; via an LCD shutter, thus avoiding moving parts; or via fibre optic light pipes for high volume testing. The mirror 530 reflects fluorescence emitted from the coin, back upwards, through the medium towards the light sensor 615. The light sensors are implemented with an imager. In one embodiment, this is a linear imager. In a further embodiment this is an area imager, allowing the light from multiple fibres to be simultaneously measured. In the embodiment of an area imager, they provide a two-dimensional model of emission from the coins. Conventionally, fiber-optic waveguides bring the light from multiple test locations so as to effectively provide a projected bar chart of wavelength vs sample. Within the RoaaaR architecture, successive images correspond to different excitation spectra and sequential thermocycle iterations. The spectra depend on the LED control and the dynamic filtering.

The preceding sections disclose the structural aspects of the microfluidic platform. Now, the various flow sequencing within the microfluidic laboratory is explained in the remainder of this disclosure in conjunction with FIGS. 7A to 7O.

Referring to FIG. 7A, the figure illustrates complete flow sequencing in the microfluidic laboratory (MFL). The MFL is based on a single-use, RNase/DNase-free microfluidic plastic moulding. It should be noted that although the MFL is single use, it has been designed to maximize the ease of recycling of its components. Reagents are injected into storage cavities in the MFL. In one embodiment, they are then desiccated by freeze-drying. In further embodiments, desiccation may be done by air-drying or other comparable techniques. After desiccation, rehydration liquids are also loaded into the MFL. The chambers containing reagents and sample materials are filled by micro-pipetting in the factory. Micropipettes are applied to micro-machined adapter ports on the MFL. By preference, capillary action is used for uptake of the liquids. This is to minimise the quantity of micro-machined ports, valves and piezo pumps needed to complete the structure. As noted above, once filled, the reagent chambers require desiccation (lyophilization) to stabilize the compounds as powder. It should be noted that lyophilization of reagents is frequently done today by manufacturers to preserve, say, a full day supply of a master mix reagents to a laboratory, however in the MFL, lyophilized samples are prepared on a single test basis within. Pure, deionized, nucleotide-free water for rehydration is injected into reservoirs in the MFL. In a specific embodiment, the empty spaces normally filled with air during lyophilization are filled with argon to inhibit oxidation and hence deterioration of the lyophilized contents.

Depending on the assay in use, a variety of microfluidic structures are used within the MFL. The various structures depicted in FIG. 7A are sampling tube 702, pump 704, multiplexer 706, one-way valve 708, sample pre-treatment reservoir 710, valve 712, recirculation valve 714, RNA extraction and concentration chamber 716 (also referred to as a piezo electric type element, electrostatic ribonucleic acid extraction and concentration unit), RNA concentration valve 718, RNA elution constant volume valve 720, RNA eluent reservoir 722, RNA eluent input valve 724, RNA elution pump 726, RNA concentration circulation valve 728, conductivity sensor 730, valve 790, valve 732, sensor 734, eluate dosing chamber 736, valve 792, valve 794, turbulent flow mixer 738, bubble removal chamber 740, analysis settling chamber 742, valve 796, reaction analyte pump 744, valve 746, bubble removal chamber 748, assay coin 750, coin fill valve 752, vent with graphite fill detection 754, assay mix rehydration liquid reservoir 756, valve 758, multiplexer 760, assay mix rehydration pump 762, analysis mix chamber with lyophilized contents 764, bubble removal chamber 766, valve 768, assay mix rehydration valve 770, valve 772, NTC water reservoir 774, valve 776, turbulent flow mixer 778, pump 780, valve 782, NTC coin 784, coin fill valve 786, and vent with graphite fill detection 784.

Acoustic pumps work on principle of piezo elements pressing on a PTFE membrane sealed over the internals face of the microlab. The membrane is pressed down—or not—by flexure of the piezo element. The pressure increase cause by the flexure causes fluid flow depending on the resistance to flow of the inlet and outlet ports of the pump.

Acoustic valves work on principle of piezo elements pressing on a PTFE membrane sealed over the internal face of the microlab. The membrane is pressed down—or not—by flexure of the piezo element. When actuated, the piezo element flexure presses on an internal seal, preventing fluid flow.

Microlab uses pressure-directed valves that use differential pressure around an orifice to act as one-way valves. Exploiting the viscosity of the bulk fluid, the liquid exhibits high pressure on the inlet, and low pressure on the outlet.

The complete flow sequencing in the MFL can be divided into two stages. A first stage of RNA extraction and concentration (depicted as dotted lines in the FIG. 7A) and a second stage of reaction of the eluate having the extracted RNA with the various reagents in the two coins, and further processing in the coins to analyze the sample. The various flow sequence is discussed in the following figure descriptions.

Figure 7C:
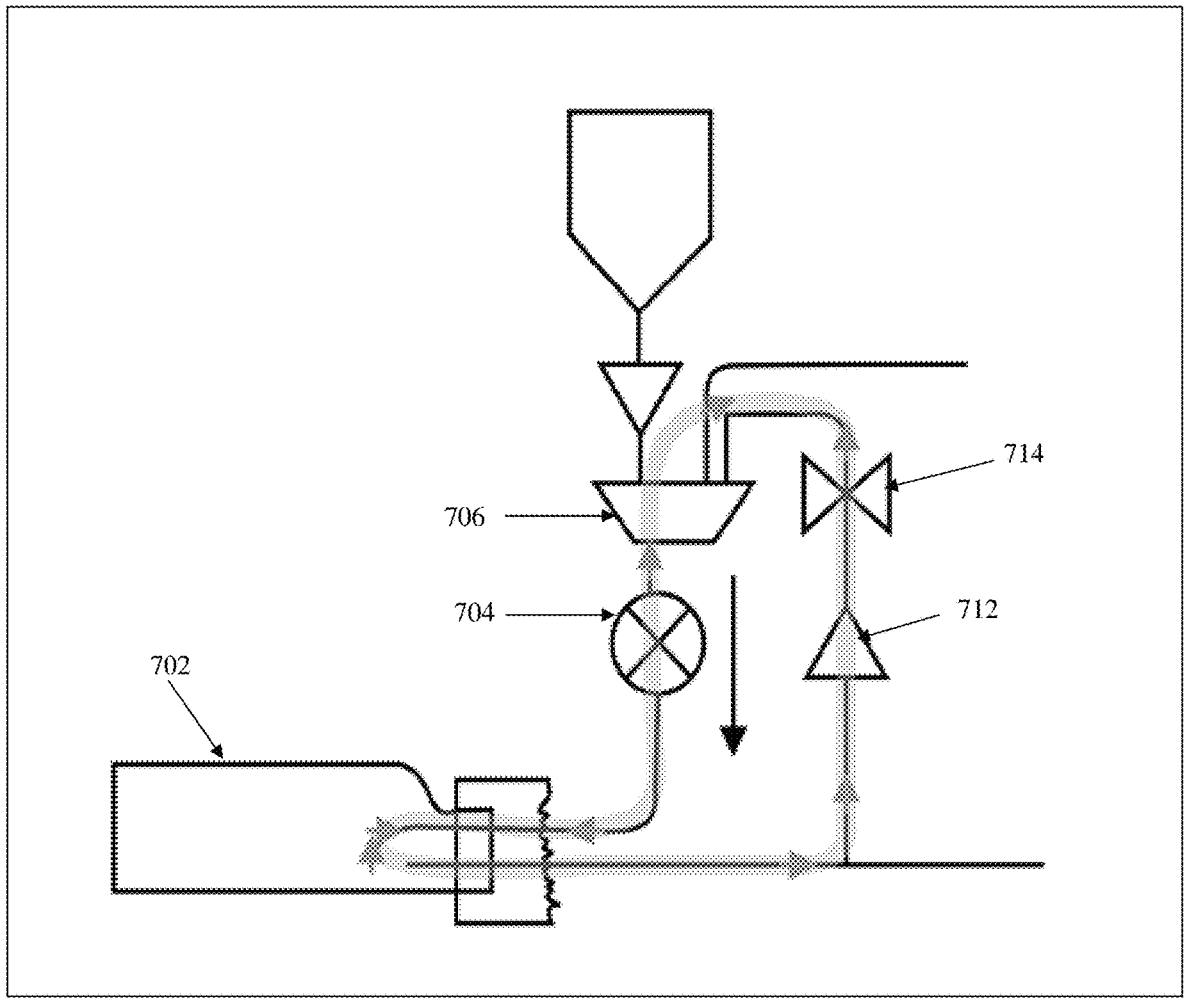
FIG. 7C illustrates pre-treatment mixing flow sequence in the microfluidic laboratory, in accordance with one embodiment of the present disclosure.

FIG. 7C illustrates pre-treatment mixing flow sequence in the microfluidic lab. The pre-treatment mixing flow sequence involves mixing the sample with the pre-treatment reagents stored in the reservoir 710 and circulating through a pre-treatment mixing loop. The flow sequence includes the sampling tube 702, the pump 704, the multiplexer 706, the valve 712, and the recirculation valve 714. To ensure the sample and pre-treatment are fully mixed, the solution is pumped back to the sampling tube for a pre-determined period. There is a likelihood of increased bubble formation, depending on the pre-treatment. If so, a bubble removal chamber may also be needed. It is to be noted that the sampling tube 702 is designed to receive excess, liberated gas.

Figure 7D:
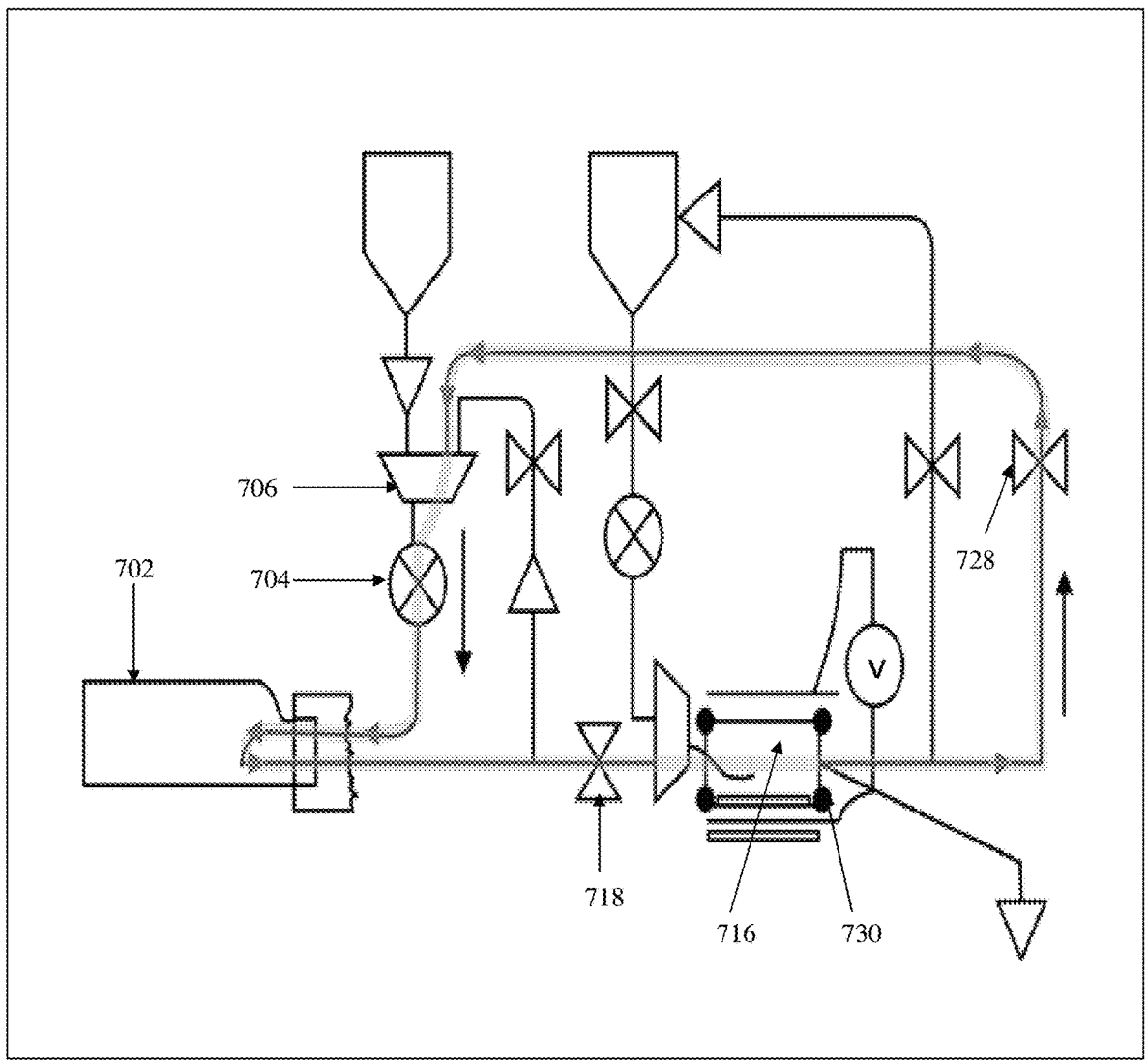
FIG. 7D illustrates an RNA extraction flow sequence in the microfluidic laboratory, in accordance with one embodiment of the present disclosure.
Figure 7E:
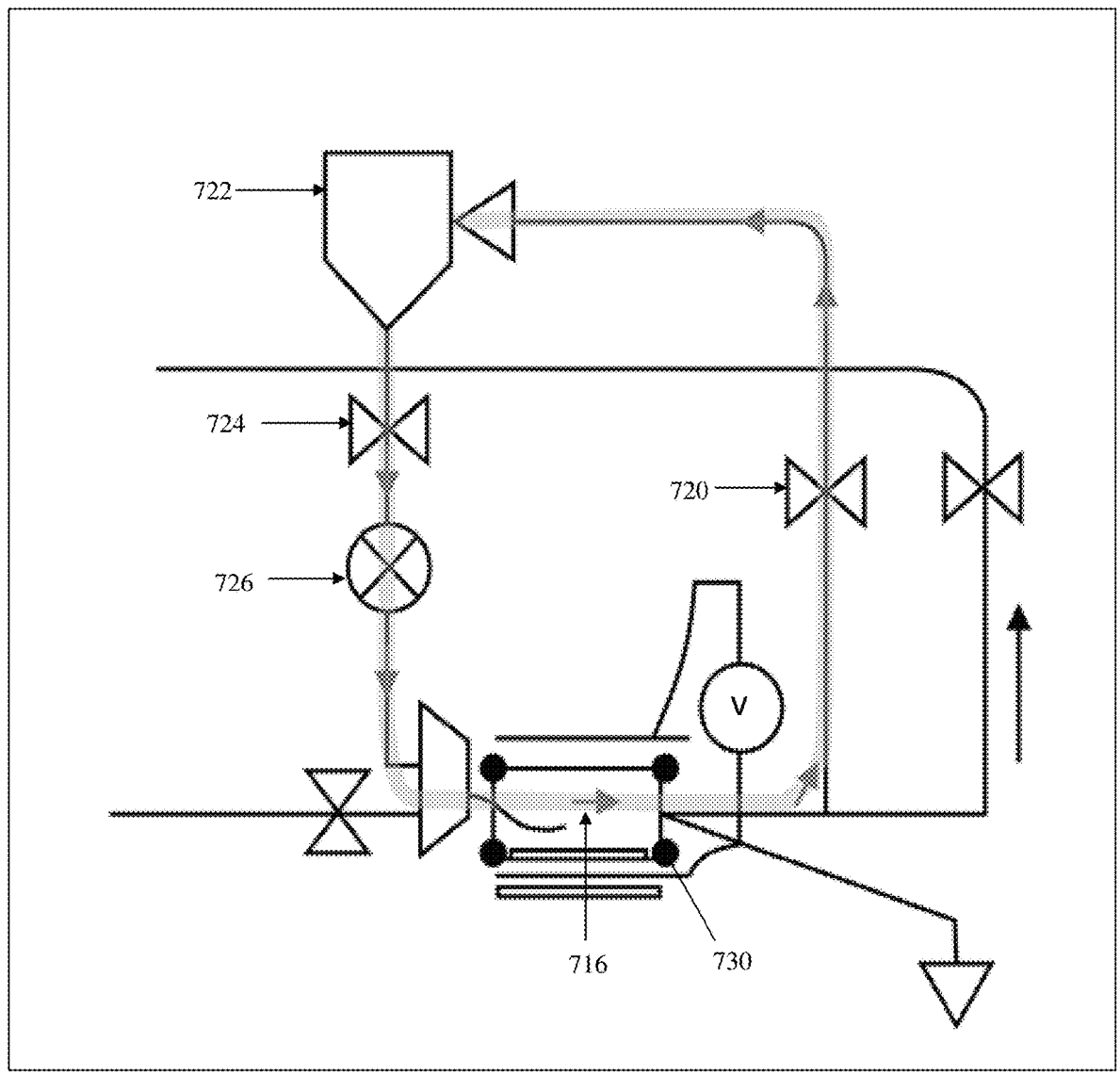
FIG. 7E illustrates an eluent flow sequence in the microfluidic laboratory, in accordance with one embodiment of the present disclosure.

FIG. 7D illustrates an RNA extraction flow sequence in the microfluidic lab. The combined and mixed sample material, optional preservative lysis buffer, and optional pre-treatment solution are pumped though the RNA extraction and concentration chamber (REC) 716. The flow sequence includes the sampling tube 702, the RNA concentration valve 718, the RNA extraction and concentration chamber 716, RNA concentration circulation valve 728, the multiplexer 706, and the pump 704. The solution passes through a route that returns it to the sampling tube, washing any remaining, accessible RNA from the tube 702. The negatively charged RNA strands are bound to an inner surface of the REC 716. A dextran coating is applied to a large area of the REC 716. It is shaped to optimize subsequent elution i.e. a low possibility of adsorbed RNA being permanently attached to the dextran. The REC 716 is a cylindrical construction with electrodes in its center and around the outside of the plastic wall. The plastic wall must be coated with dextran and a binder to electrostatically attract and secure the virus RNA liberated into lysate by the lysis buffer in the sampling tube 702. The cylindrical chamber walls are textured to provide the largest surface area possible, consistent with not damaging the RNA, and compatibility with subsequent use of eluent to liberate the RNA. The cylindrical chamber optimizes the available area for adsorption and facilitates eventual removal of the extracted RNA from the bound surface by both chemical and electrical means. It is then further concentrated before delivery to the dosing chamber 736. The RNA extraction and concentration chamber 716 in the microfluidic laboratory is further explained in conjunction with FIG. 7B.

The purpose of REC 716 is to acquire every molecule of RNA present in the sample. Typically, the viral particle counts may be low. A count of 3 copies/μl is vulnerable to inadequate lysis buffer mixing, contamination by rogue RNA or the presence of RNase or DNase. Two means of RNA concentration are accommodated: the addition of a custom, third party chemical attractant and by applying a high voltage, modulated electrical field. RNA is electrically polarized. It's electric field over short molecular distances may amount to many kV/m. The RNA extraction method uses polarization to draw RNA molecules toward a preferred location in the REC 716. Distances through the microlab are far greater than molecular bond distances, by many orders of magnitude. Nonetheless, even with macroscopic distances of ~0.5 to 1 mm, an externally applied voltage of ~400V will still provide a field of ~40 kV/m. This will induce a molecular drift towards the anode. The SARS-CoV-2 virus has a genome of 30,000 bases, so its molecular weight will be large, and hence the molecular drift velocity of will be much slower than say, the interaction with primers. It should be noted the primer target sequences are selected in part for their optimal robustness compared to surrounding sequences. Consequently, the possibility of breaking a sequence of interest is probably lower than the average of all possible sequences of comparable lengths in the genome. The effect of application of an external electrical field with RNA will be greater than DNA because the latter mechanically stabilizes itself. Still, as the molecule interacts with itself and surrounding molecules, it will not manifest as a straight line. However, for every exposed hydrogen bond, it will form a dipole with the remainder of the structure. That overall dipole will still interact with the applied field, applying a rotational moment. It is possible the potential energy of the rotation will fragment the RNA. In the use case of SARS-COV2 detection, the primers do not select for a sequence in excess of 100 bases, so the chance risk of a complete strand being fragmented in a region of interest is less than 1 in 300, implying a strand in an area of interest in 1 in 900 samples can be broken if the limit of sensitivity is 3 virus particles. The application of external high voltage electrical fields will be via electrodes in the metal structure surrounding each microlab during processing. In one embodiment, the metal structures are integrated to the microlab. High voltages are generated locally to the point of application to remove safety concerns. The high voltage generation is achieved by configuring a local microcontroller to set a reference voltage to be matched by a switched-mode, dc-dc converter. The available current is restricted to 1 μA although this is for safety purposes and not otherwise an essential aspect of the disclosure. Using this, voltages in the range 100V to 400V are typical, although in various embodiments, higher or lower voltages may also be used. Higher voltages produce shorter extraction periods.

Referring to FIG. 7B, material from the sampling tube—sample plus lysis buffer—is pumped through the REC 716. The REC 716 has two exit ports. The intention is that one has a high volume output, the other is low volume output. This requirement arises from the necessity of pumping the sample material round the loop several times in as short a period as is practical. With a total capacity of 2 ml of sample plus lysis buffer, five loops of the flow demand a flow rate of 170 μl/s is required. This is a flow rate likely to damage RNA if the channel diameter is narrow, so a larger diameter route must be provided. Considering the REC 716 as largely cylindrical, a positive bias voltage is applied to a collar 7902 around the REC 716 with respect to a wire passing through the axial centre of the cylinder. This must be dimensioned according to the flow rate required during circulatory pumping. The bias establishes an electric field causing negatively charged RNA to migrate to the cylinder wall for adsorption. In a particular embodiment with particularly fragile RNA, depending on the intended target genes, it may be necessary for the axial wire to be surrounded by a thin plastic sheath if direct metal contact with the liquid would degrade the RNA. The external electric field is applied with the positive plate outside the optionally dextran-coated cylinder wall. For maximum effect, the REC wall should be as thin as possible. The negative electrode is a thin, inert wire passing up the centre of the cylinder. This approach minimizes the opportunity for RNA strands to be wasted. A cylindrical chamber permits all the available area to be coated with dextran whilst facilitating the applied bias voltage. In any case, the REC should not be rectangular i.e. with corners that may trap and render inaccessible RNA strands. Typically, the distribution of RNA along the length of the cylinder will not be uniform. The finite drift velocity will be proportional to the applied voltage, and RNA density will be greater further away from the inlet. It may be advantageous to have the inlet have a deflector 7900 to direct material towards the walls of the cylinder as it enters. A complementary structure at outlet would cause liquid close to the cylinder wall to not be recirculated. Exploiting laminar flow, the liquid close to the wall would remain there. Only the liquid travelling down the center of the cylinder would be recirculated using an RNA concentration recirculation port 7908. This would help minimize RNA molecules which have only partially migrated being swept out again. The output deflector 7906 is a torus. Material outside the torus is deflected towards the cylinder walls and the adsorption material. Note there is no such material directly adjacent to the torus. This is to prevent RNA facing a longer path length for subsequent concentration. After a period considered appropriate to extracting all the RNA, the electrical bias is reversed, and eluent is pumped into the REC 716. An optional piezo-acoustic vibration agitator 7904 assists the eluent in liberating RNA from the cylinder wall. The liberated RNA migrates towards the axial wire. The REC 716 needs to be sufficiently long for the migratory drift to take effect and be complete. The total volume of eluent will be far greater than the amount required for the reaction chamber. To migrate the RNA into a more compact region the electric field is reoriented towards the vertex of a conical feature within the chamber. The feature terminates in a metering channel. When sufficient time has elapsed for the vertex to contain all the RNA, a valve is opened allowing the RNA-laden eluant to pass through. Electrical conductivity changes are measured when the metering channel is full and is measure using conductivity sensor 730 along the elution dosage channel 7916. The voltages applied to the primary 7910, secondary 7912, and dosage electrodes 7914 are phased to progressively migrate the RNA molecules towards the output volume of the chamber at high speed. The actual voltages and timing will be subject to calibration for specific target sequences. For that reason, the voltage set points and their timing must be under software control, with the actual values available in the Cloud and in the non-volatile memory. Of greatest importance is the surface finish of the REC 716. There must be the maximum possible area for adsorption, consistent with the RNA molecule dynamics. After a pre-determined period, RNA concentration stops.

FIG. 7E illustrates an eluent flow sequence in the microfluidic lab. The flow sequence includes RNA concentration chamber 716, RNA elution valve 720, RNA eluent reservoir 722, RNA eluent input valve 724, and RNA elution pump 726 in the recirculation path. The eluent is stored in the reservoir 722. As depicted, it is expected the eluent will be in liquid form and may be sustained as such over the temperature range demanded by the storage and operating conditions of the MFL. If the eluent is to be in lyophilized form, a further stage of rehydration will be needed. Note the use of carbon sensors which are essentially conductivity sensor 730 to determine when the eluent has filled the REC 716. It is to be noted that the circular dots depicted on reservoirs, chambers and flow sequences indicates the conductivity sensors. Excess liquid in the REC 716 circulates into the eluent reservoir 722 but pumping stops when the REC 716 is filled with eluent. This is for the purpose of minimising the risk of discarding RNA strands. Graphite is an excellent adsorption substrate which might attract the analyte. Care must be taken to avoid a significant adsorption surface. Sensing current will typically be less than 1 μA, with a duty cycle of typically not more than 1%. As depicted the eluent is pumped into the REC 716. The flow path is shown as continuing back round to the eluent reservoir 722. However, that is not the action. When the pumped eluent has filled the REC, it will have displaced the original sample solution. It is possible, although unlikely an original virus particle has through incomplete mixing survived lysis and the other stages up until this point. It is essential that particle is not ejected into the environment. So, the elution process is a closed loop, and material forced through the flow channels, displaced by the eluent back into the eluent reservoir 722. This imposes a volume relationship between the various chambers. The eluent reservoir must be able to accommodate the expected ejecta from the flow channels without exerting excessive back-pressure into the REC 716. Electrical connection to these is provided on the integrated printed circuit board (PCB). The supporting electronics in the RoaaaR instrument senses the change in conductivity associated with eluent in contrast with lysis buffer and a range of saliva characteristics. When the conductivity between all combinations of carbon rods satisfies the expectation of eluent, there is no further filling of the REC 716.

When the REC 716 is full of eluent, two actions take place:
1. The piezo elution agitator 7904 shakes the REC 716, assisting the eluent in liberating the RNA from the surface of the dextran. The optimal frequency and amplitude necessary to affect this action is characterized for specific RNA or DNA molecular weights. The bias voltage generator output is galvanically isolated from the remainder of the system. However, it may be necessary to have 0V of the high voltage bias be connected to the 0V of the REC piezo agitator 7904. This is an implementation detail that does not affect the universal application of this disclosure.
2. The polarity of the bias voltage is reversed, ejecting the RNA and any other negatively charged ions or molecules away from the dextran surface. Here, the advantages of a cylindrical REC become apparent. Liberated molecules will drift toward the positive electrode which at this time, is in the center of the cylinder. After a period to be determined, the piezo vibration is stopped. The RNA elution concentration valve 728 is closed, and the valves (valve 790, valve 732) into the eluate dosing chamber 736 is opened, leading to the next phase as depicted in FIG. 7F.

Figure 7F:
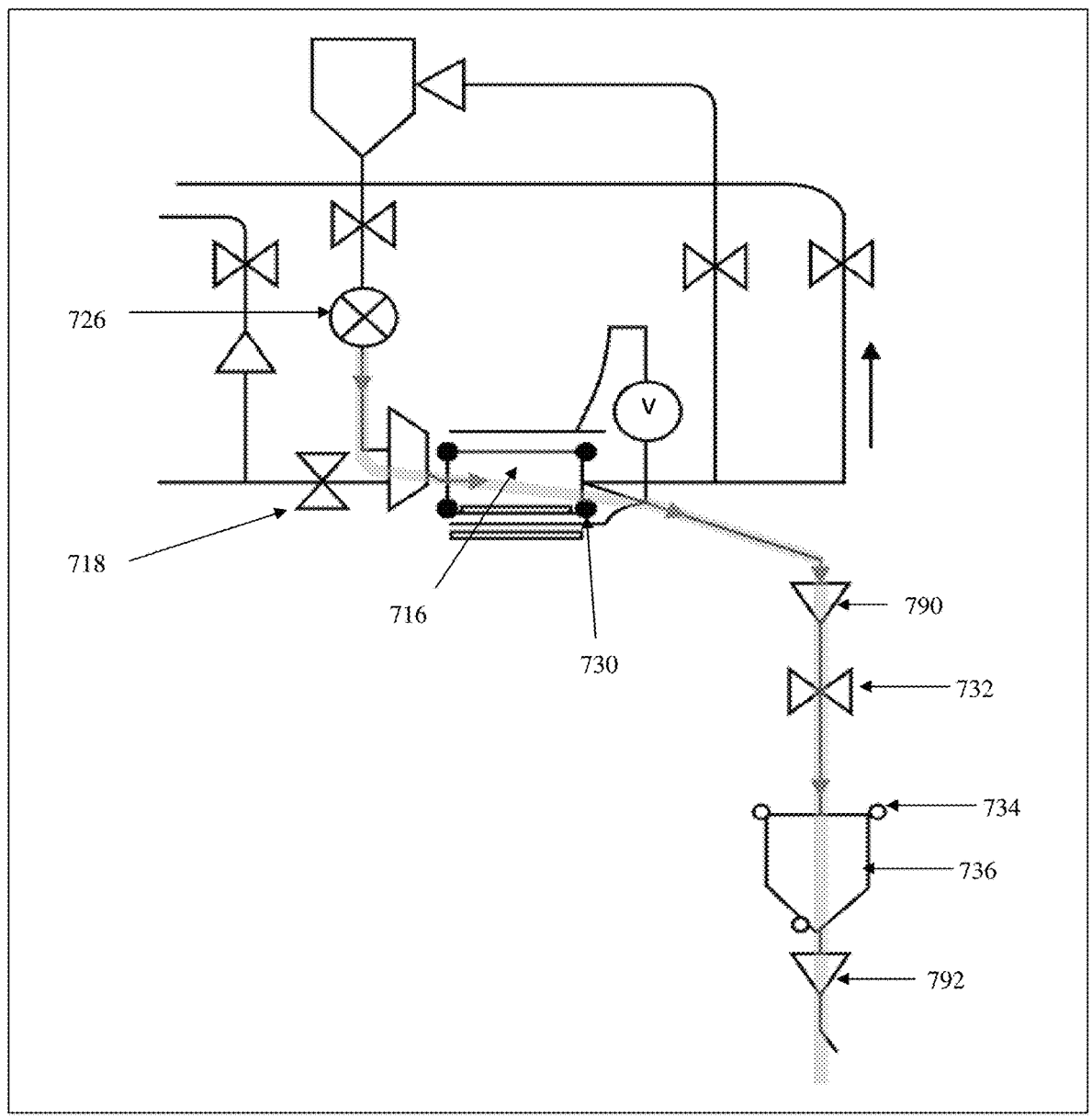
FIG. 7F illustrates an eluent metering transfer flow sequence in the microfluidic laboratory, in accordance with one embodiment of the present disclosure.

FIG. 7F illustrates an eluent metering transfer flow sequence in the microfluidic lab. The RNA elution pump 726 pushes the eluate into the dosing chamber 736. Carbon rods/sensors 734 are used to facilitate electrical determination of the chamber 736 becoming filled.

Figure 7G:
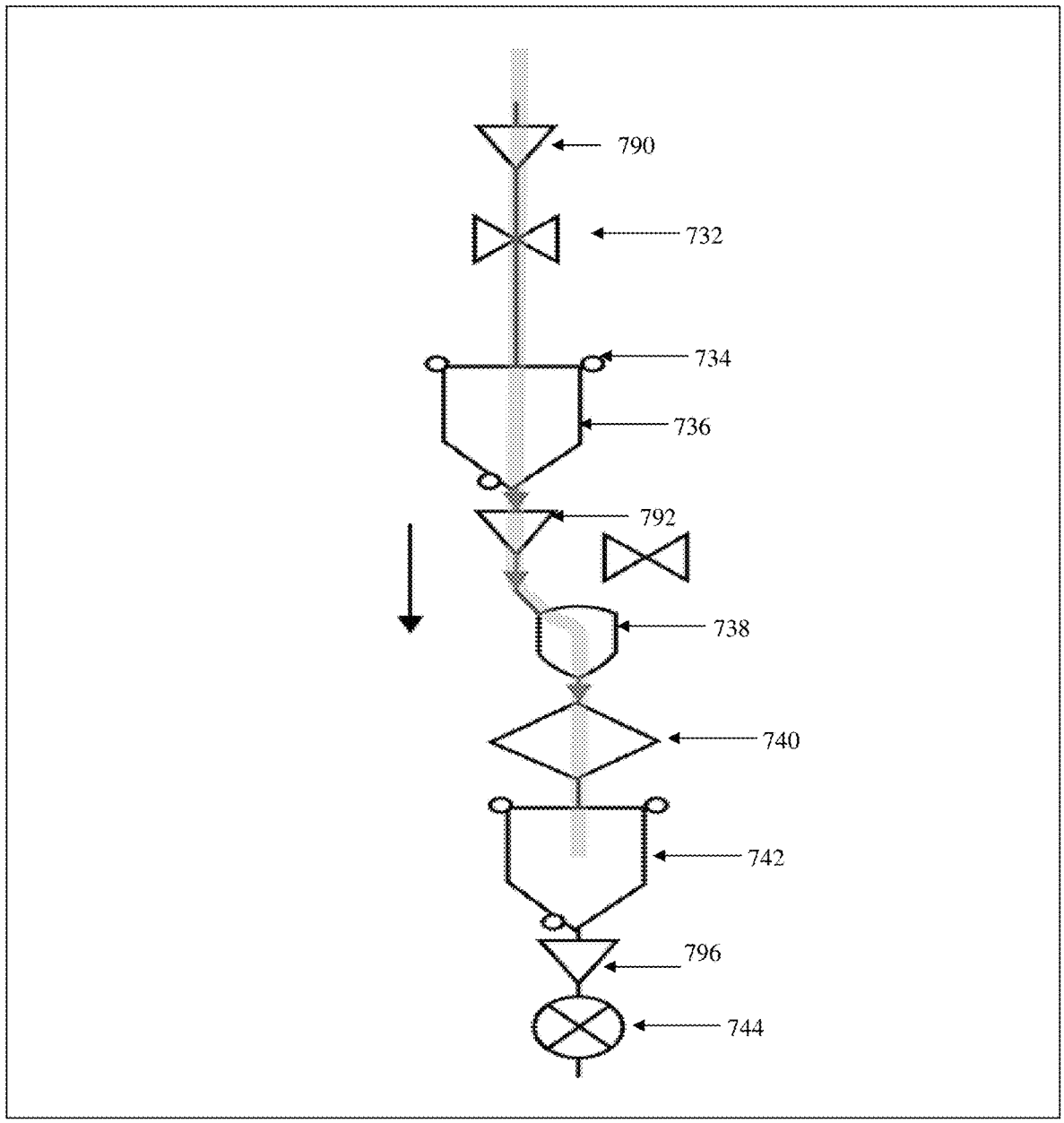
FIG. 7G illustrates an eluate dose transfer flow sequence in the microfluidic laboratory, in accordance with one embodiment of the present disclosure.

FIG. 7G illustrates an eluate dose transfer flow sequence in the microfluidic lab. Eluate dose transfer flow sequence involves the valve 790, valve 732, eluate dosing chamber 736, valve 792, turbulent flow mixer 738, bubble removal chamber 740, and the analysis settling chamber 742. With the proper eluate dose obtained, it is pumped into the analysis/assay settling chamber 742. This has sufficient capacity for the eluate plus the reagents. Consequently, bubble formation is inevitable and is removed using the bubble removal chamber 740. In the next stage, eluate and reagents are combined as depicted in FIG. 7H.

Figure 7H:
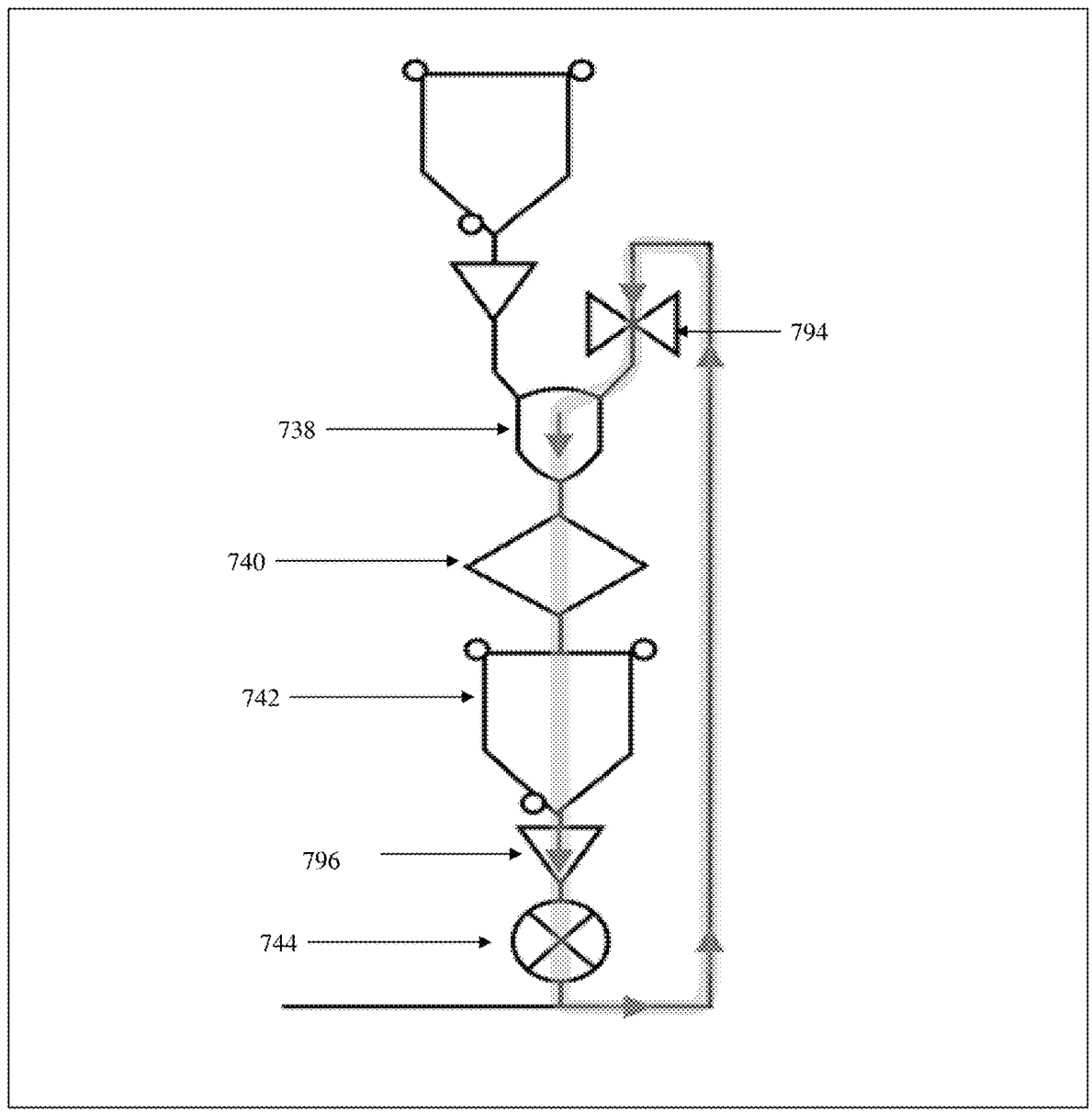
FIG. 7H illustrates reaction dose mixing flow sequence in the microfluidic laboratory, in accordance with one embodiment of the present disclosure.

FIG. 7H illustrates reaction dose mixing flow sequence in the MFL. Reaction dose mixing flow sequence involves valve 794, turbulent flow mixer 738, bubble removal chamber 740, the analysis settling chamber 742, valve 796, and pump 744. The dose of eluate and rehydrated master mix are combined through one of more cycles of turbulent flow mixing followed by bubble removal. Turbulent mixing involves passing two or more materials simultaneously through the mixer. The internal spikes cause turbulent flow, mixing the constituents whilst simultaneously removing bubbles.

Figure 7I:
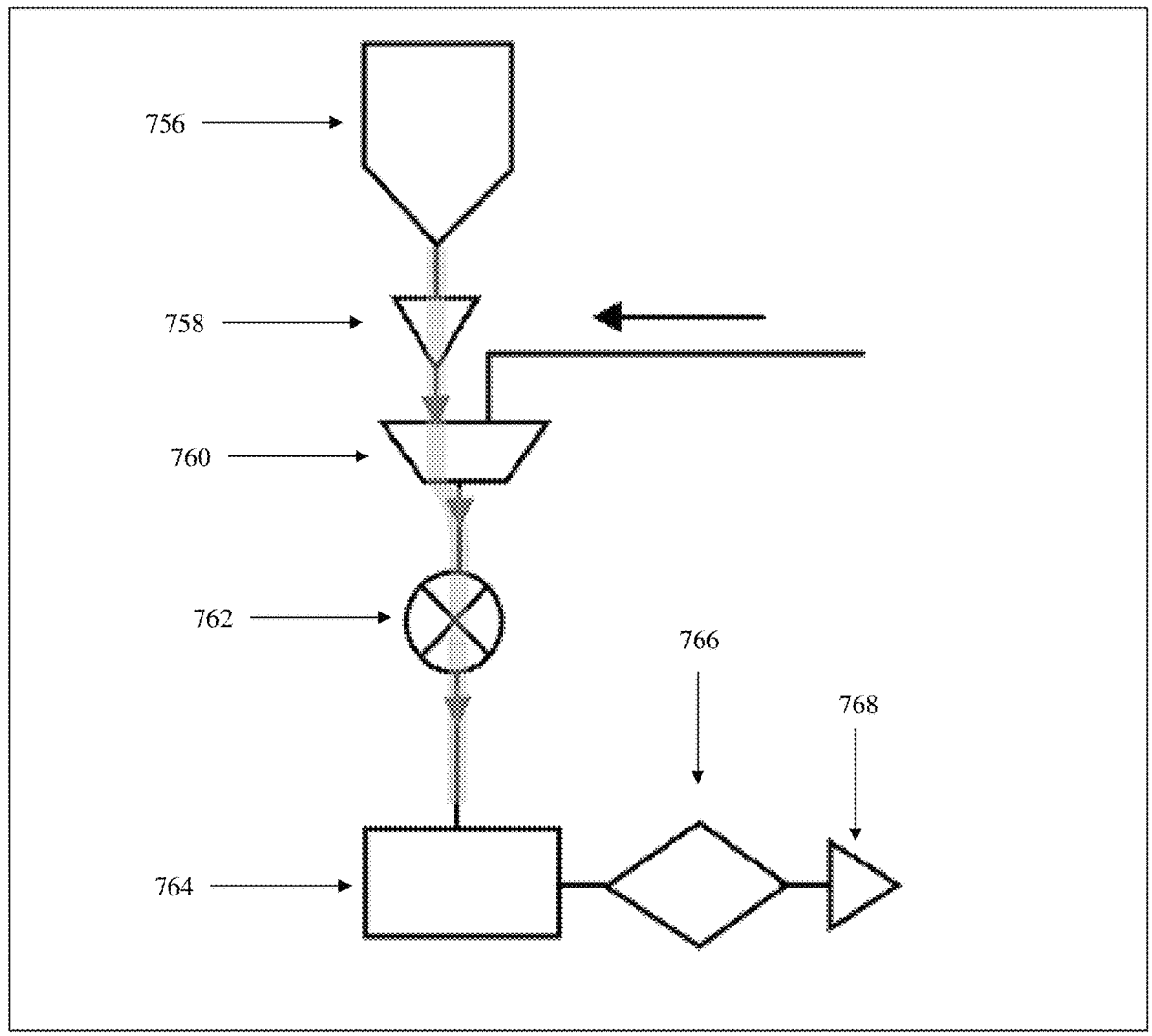
FIG. 7I illustrates a reagent rehydration input flow sequence in the microfluidic laboratory, in accordance with one embodiment of the present disclosure.

FIG. 7I illustrates a reagent rehydration input flow sequence in the microfluidic lab. Reagent rehydration input flow sequence involves assay mix rehydration liquid reservoir 756, valve 758, multiplexer 760, assay mix rehydration pump 762, analysis mix chamber with lyophilized contents 764, bubble removal chamber 766, and valve 768. Central to the entire RoaaaR technology is the use of lyophilized reagents (a one-step mix of reverse transcriptase, primers/probes, compatible controls, passive control, dNTP and buffers). These must be rehydrated before use. The rehydration liquid reservoir 756 contains the exact amount for rehydration.

Figure 7J:
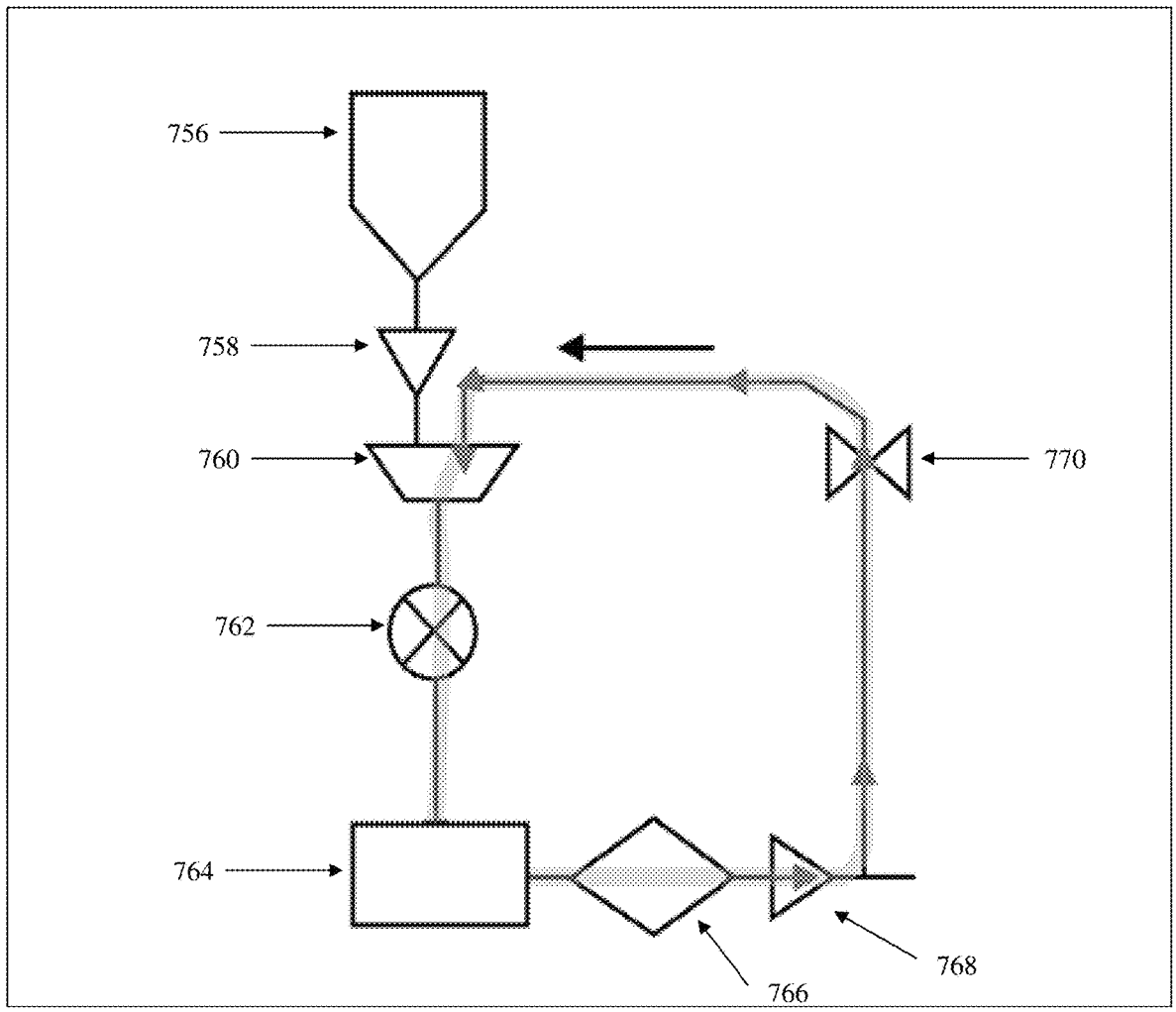
FIG. 7J illustrates a rehydration recirculation flow sequence in the microfluidic laboratory, in accordance with one embodiment of the present disclosure.

FIG. 7J illustrates a rehydration recirculation flow sequence in the microfluidic lab. Rehydration recirculation flow sequence involves the multiplexer 760, assay mix rehydration pump 762, analysis mix chamber with lyophilized contents 764, bubble removal chamber 766, valve 768, and assay mix rehydration valve 770. With the rehydration liquid in the mix chamber 764, the resultant solution is repeatedly pumped around and through the chamber 764 to ensure an even mix. Bubbles are removed via a bubble removal chamber 766.

Figure 7K:
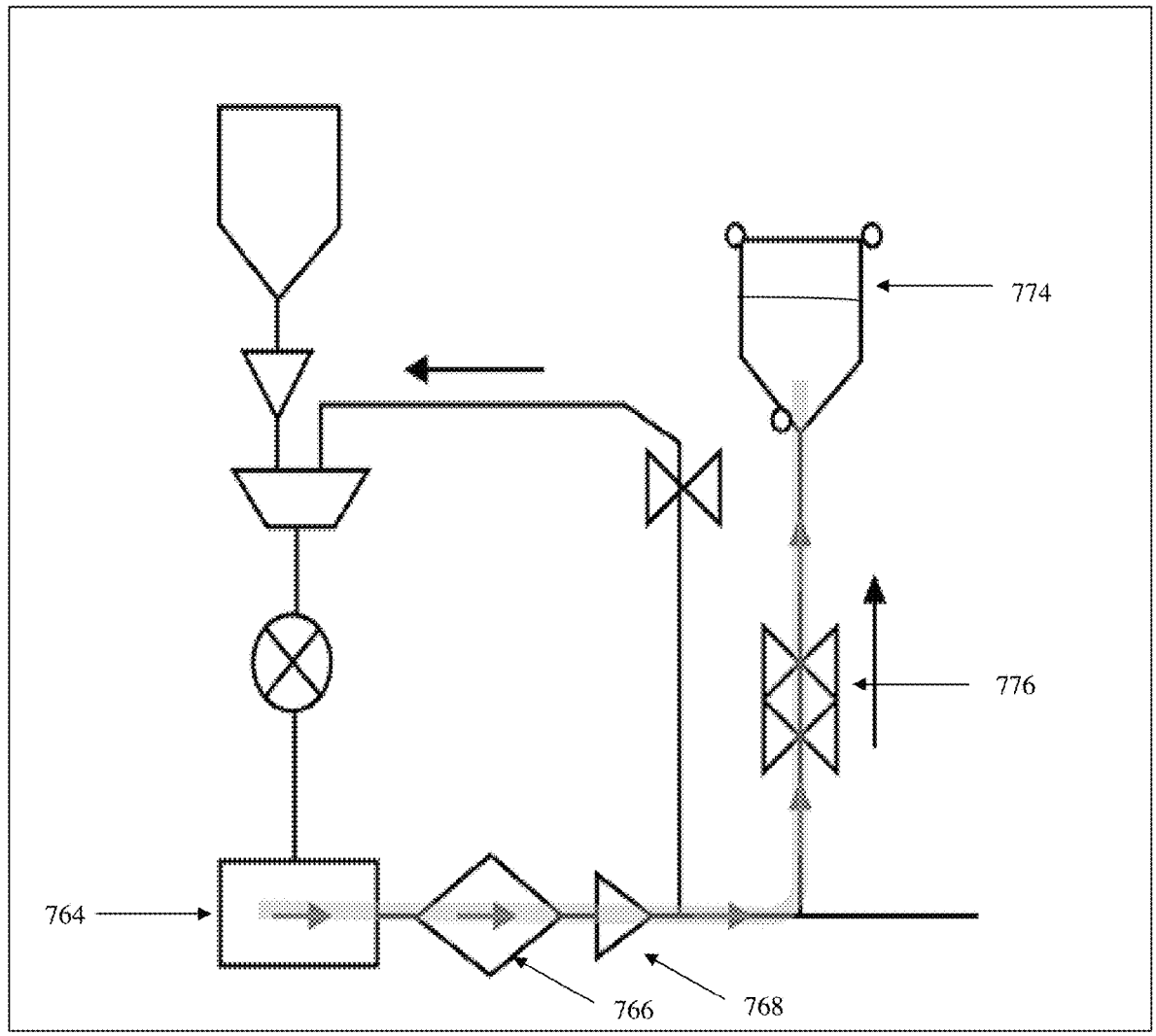
FIG. 7K illustrates master mix input flow sequence in the microfluidic laboratory, in accordance with one embodiment of the present disclosure.

FIG. 7K illustrates master mix input flow sequence in the microfluidic lab. The master mix input flow sequence involves analysis mix chamber with lyophilized contents 764, bubble removal chamber 766, valve 768, NTC water reservoir 774, and valve 776. The NTC coin is filled with a combination of the rehydrated reagents, but with nucleotide-free ('no-target') water. The NTC water reservoir 774 is pre-filled in the factory, but only partially. The remaining gap is the exact amount to be filled with rehydrated assay mix which passes through another double valve 776. Carbon rods (marked in circles) on the reservoir 774 are used to assess completed filling.

Figure 7L:
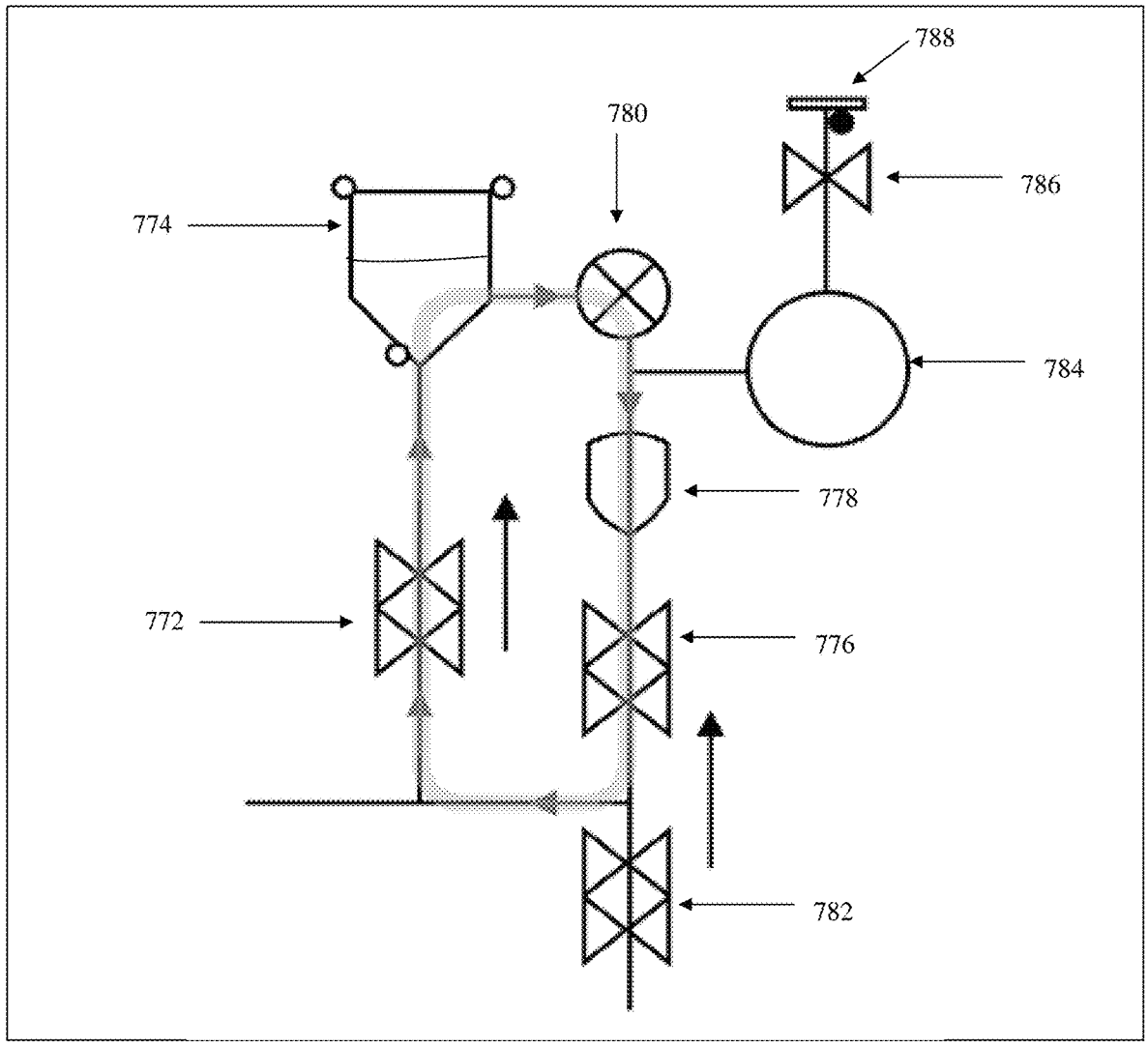
FIG. 7L illustrates the master mix homogenization flow sequence in the microfluidic laboratory, in accordance with one embodiment of the present disclosure.

FIG. 7L illustrates the master mix homogenization flow sequence in the microfluidic lab. The homogenization of the NTC water and assay mix is carried out through the loop having valve 772, NTC water reservoir 774, pump 780, turbulent flow mixer 778, and valve 776.

Figure 7M:
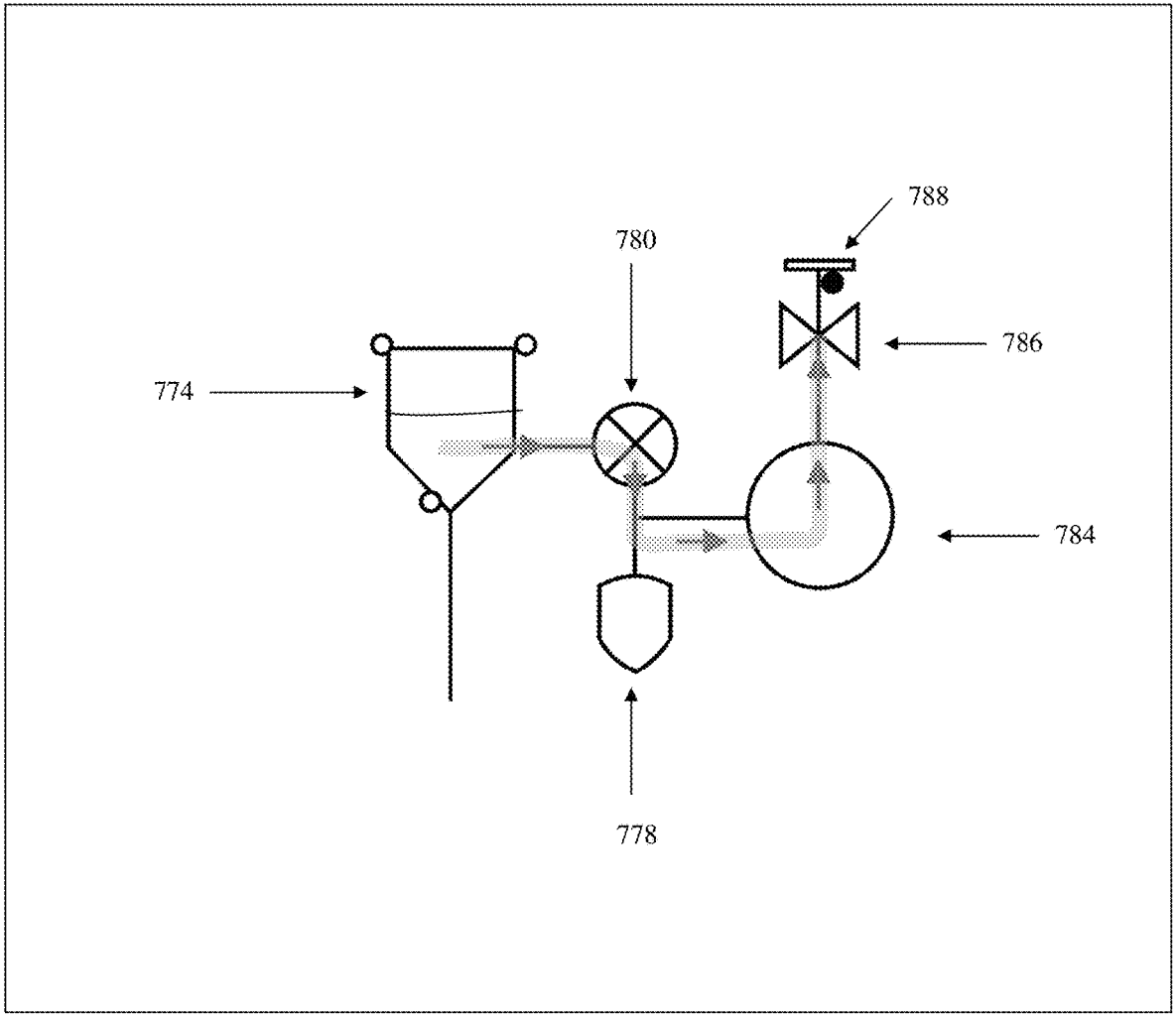
FIG. 7M illustrates NTC coin loading flow sequence in the microfluidic laboratory, in accordance with one embodiment of the present disclosure.

FIG. 7M illustrates NTC coin loading flow sequence in the microfluidic lab. The NTC coin loading sequence involves NTC water reservoir 774, pump 780, and NTC coin 784, coin fill valve 786, and vent with graphite fill detection 788. The vent returns gasses to the sampling tube.

Figure 7N:
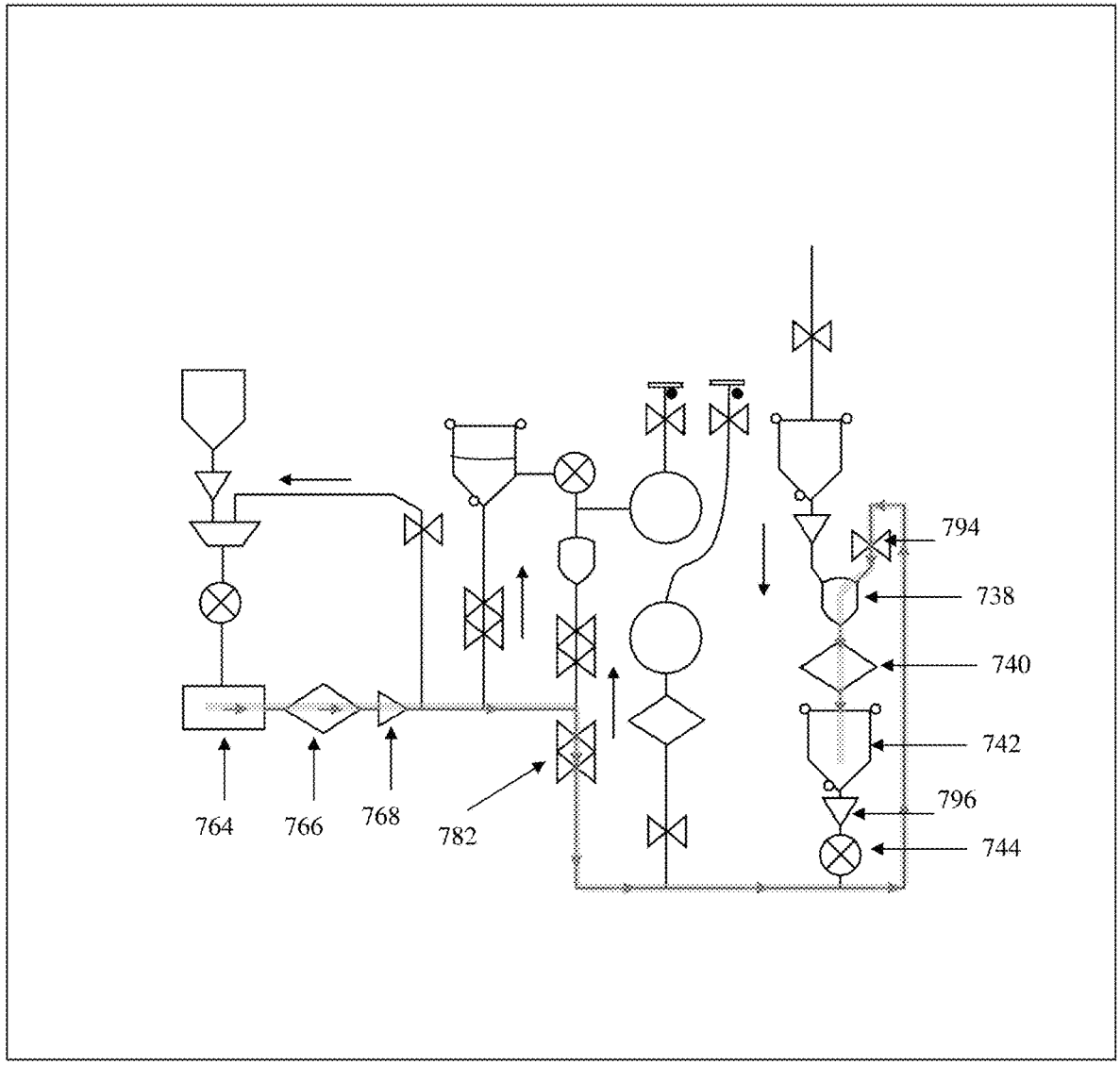
FIG. 7N illustrates master mix transfer flow sequence in the microfluidic laboratory, in accordance with one embodiment of the present disclosure.
Figure 7O:
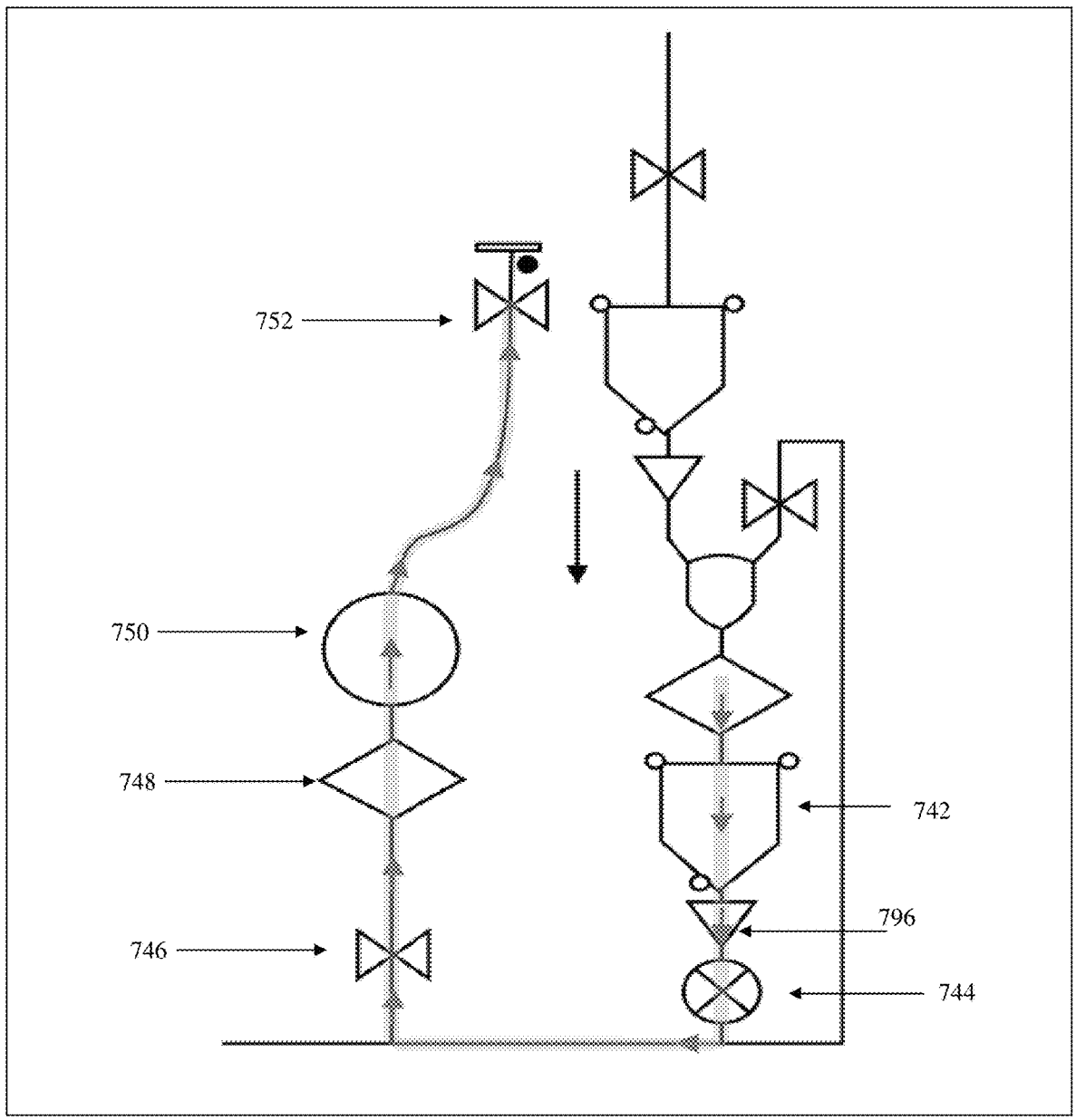
FIG. 7O illustrates assay reaction cell coin loading flow sequence in the microfluidic laboratory, in accordance with one embodiment of the present disclosure.

FIG. 7N illustrates master mix transfer flow sequence in the microfluidic lab. The master mix transfer flow sequence involves analysis mix chamber with lyophilized contents 764, bubble removal chamber 766, valve 768, valve 782, valve 794, turbulent flow mixer 738, bubble removal chamber 740, analysis settling chamber 742, valve 796, and reaction analyte pump 744. Through a double valve 782, to eliminate contamination, the rehydrated reagent mix is injected into the analysis settling chamber 742 prior to circulatory mixing. The eluate must be injected beforehand to ensure the correct volumetric total. The chamber 742 volume must accommodate the final reaction volume plus losses in the connecting channels. Carbon sensors are used to measure the conductivity of the settling chamber contents and to check whether it is full. Bubbles must be prevented, and they are removed using bubble removal chamber 740.

FIG. 7O illustrates assay coin loading flow sequence in the microfluidic lab. The assay coin loading sequence involves analysis settling chamber 742, valve 796, reaction analyte pump 744, valve 746, bubble removal chamber 748, assay coin 750, coin fill valve 752, and vent with graphite fill detection 754. Once the reaction mix is complete, it is transferred into the assay coin 750 for thermocycling. It may be necessary to add a further bubble removal chamber 748. The assay coin 750 is vented to prevent gas back pressure from preventing filling. As previously described, this is best vented into the sampling tube. However, it must be absolutely ensured no contamination, particularly aerosol, must be allowed to push back into the coin vent 754.

The microfluidic platform presented in the disclosure has several advantages, it provides rapid, high volume, low cost, accurate mass screening for SARSCoV2 infection. It provides high speed testing. In one example, 144 tests/day for minimal configuration can be carried out, in another example, >30,000/day in larger formats with multiple racks in a single system can be carried out. In all systems, 60 tests/rack/hour using standard protocol can be tested. The microfluidic platform provides rapid diagnostic results. Results can be published in 15 minutes using standard protocol, and as rapidly as 7.5 minutes using an accelerated protocol. The microfluidic platform is scalable. It is suitable for centralized public health use or Point-of-Care e.g. factories, offices, schools, hospitals, public transport, etc. They can be used in airports, where passengers will require the highest possible sensitivity and specificity of testing of their fellow passengers with whom they will be sharing air. It is accessible as the integrated sampling tube and micro-fluidic laboratory eliminates cross contamination and is usable in almost any situation: manual or automated sample handling. Other advantages are minimal training needed and no requirement of skilled persons with PhDs, or medical doctors or nurses. Another advantage is that it is biologically safe: No need for biological safety cabinets nor even a laboratory setting. Apart from Covid-19, this system can be used for simultaneous processing of different assays, chemistries for different pathogens—even multiple pathogens per person.

In one embodiment, a reverse transcriptase quantitative polymerase chain reaction based analyzing system comprises a sampling tube. The sampling tube comprises a tube portion, a cap coupled to the tube portion via a ratchet locking mechanism, wherein the cap comprises a closure optical detection pattern, and a radio frequency identification (RFID) tag disposed between the cap and the tube portion. The act of closure of the cap is unidirectional and cannot be undone other than by destruction. Further, the closure of the tube is inspected by using the RFID tag.

The system includes a microfluidic processing unit coupled to the sampling tube, wherein the microfluidic processing unit comprises a piezo electric type ribonucleic acid extraction and concentration (REC) unit coupled to the sampling tube via a plurality of sample flow control devices, an eluent storage unit coupled to the piezo electric type ribonucleic acid extraction and concentration unit via a plurality of eluent flow control devices, an eluate dosing chamber coupled to the piezo electric type ribonucleic acid extraction unit via a plurality of eluate flow control devices, an analysis settling chamber coupled to the eluate dosing chamber, an assay rehydration unit coupled to the analysis settling chamber via a plurality of assay control devices, an assay analysis unit coupled to the analysis settling chamber and a no-target control analysis unit coupled to the assay rehydration unit for the purposes of applying a negative control to the biological assay and simultaneously calibrating the optical metrology system by the provision of passive dyes that will be present in effectively the same quantities in both the no-target control and the biological sample, wherein the use of lyophilization in the factory to leave the required reagents in the allocated chambers of the microfluidic laboratory or microfluidic processing unit, wherein the final stage of preparation prior to calibration involves displacing the air in the channels and chambers by argon in order to dispel oxygen that might otherwise facilitate gradual deterioration in the regents by oxidation. Within this embodiment the purpose of the RFID tag within the cap is to facilitate rapid central laboratory use of the system. Within central laboratories, valuable time is lost wherein skilled technicians must open shipping envelopes or other containers in a biologically secure environment in case the sampling tube within has not been properly closed, and pathogens have contaminated the inner volume of the shipping envelopes or containers. The REC unit includes a high volume exit port and a low volume exit port. The REC unit is cylindrical and comprises an input deflector at inlet to direct material towards walls of the REC unit cylinder as it enters. The REC unit comprises a collar around and a wire passing through axial center of the cylinder. The REC unit comprises a torus output deflector to deflect material towards cylinder walls when positive biased, wherein the cylinder walls have maximum possible area for adsorption. The REC unit comprises a piezo-acoustic vibration agitator to assist eluent in liberating RNA from the cylinder walls when negative biased. The REC unit comprises an RNA recirculation port to recirculate the liquid travelling down the center of the cylinder. The REC unit comprises primary electrode, secondary electrode, and dosage electrode to progressively migrate RNA molecules towards output of the piezo electric type element, electrostatic ribonucleic acid extraction and concentration unit at high speed.

The assay analysis unit and the no-target control analysis unit are reaction chambers where a master mix of reagents, mix with extracted RNA. The reaction chambers include thermistors, heat pump, heat sink, mirror, and a lens mechanism. The system comprises an optical subsystem, wherein the optical subsystem comprises one or more light sensors, filters, and a mirror integrated to the reaction chambers. The system is configured to reduce optical noise and biological noise, to improve signal to noise ratio.

In another embodiment, a method for analyzing a biological sample, using a reverse transcriptase quantitative polymerase chain reaction analyzing system includes receiving a sample within a tube portion of a sampling tube, coupling a cap of the sampling tube to the tube portion via a ratchet locking mechanism, depositing a microfluidic laboratory comprising the sampling tube in an analytic cell (AC), wherein AC is an analytical process environment, wherein the AC may be just a single unit or may be one of a number assembled in a row; wherein a row of ACs, known as a RandOm-Access Analytical (RoaaaR) Array may be a singular unit or may be one of many housed within an outer chassis, wherein the deposition is by way of either manual insertion or robotic assignment of individual sampling tubes and microfluidic laboratories into vacant ACs; wherein asynchronous, simultaneous processing of sampling tubes integrated with microfluidic laboratories whereby each sample test commences as soon as it is inserted into an AC; wherein a control system to maintain asynchronism between assays in progress such that the optical metrology system is kept in constant use without delaying any given assay; wherein a signal detection mechanism using modulation of the excitation light correlated with both the spectrum and the intensity of individual wavelengths in the emission spectra to reduce electrical, electronic, optical and biological noise; wherein use of same modulation of the excitation light as a means of multiplexing by way of time division multiplexing (TDM) emissions from two or more ACs to economically use the same optical metrology system. The method includes checking, by a detection sensor, a locking of the cap to the tube portion, mixing a lysis buffer with the sample within the sampling tube to generate a lysated sample within the sampling tube via a mixing unit, circulating the lysated sample from the sampling tube to a piezo electric type element, electrostatic ribonucleic acid extraction and concentration unit via a plurality of sample flow control devices, separating ribonucleic acid strands from the lysated sample within the piezo electric type element, electrostatic ribonucleic acid extraction and concentration unit, circulating an eluent between an eluent storage unit and the piezo electric type element, electrostatic ribonucleic acid extraction and unit, extracting the separated ribonucleic acid strands, using the eluent from the piezo electric type element, electrostatic ribonucleic acid extraction unit and transferring an eluate comprising the extracted ribonucleic acid strands to an analysis settling chamber via an eluate dosing chamber and a plurality of eluate flow control devices, mixing a portion of master mixture from an assay rehydration unit with the eluate within the analysis settling chamber, transferring a first portion of the master mixture and the eluate to an assay analysis unit to analyze mixture of the portion of the master mixture and the eluate to diagnose a biological condition associated with the sample, transferring a second portion of the master mixture from the assay rehydration unit to a no-target control analysis unit to perform a no-target control analysis of the second portion of the master mixture, performing uniform (isothermal) or varying temperature control of the reverse transcriptase, quantitative polymerase chain reaction (RT-qPCR) assay or any other assay chemistry benefitting from the high accuracy, contaminant-free, optical detection methods, providing asynchronous processing of the collection of simultaneous assays in a system to minimize the test extraction periods and share the more costly resources such as the optical subsystem between assays without slowing individual assays and equipping individual microfluidic laboratories with mirrors underneath their reaction chambers to maximize the available emitted fluorescence, approximately doubling the light at each stage and for qPCR or RT-qPCR, reducing the cycle count by one. The step of extracting the separated ribonucleic acid strands includes deflecting material towards the cylinder walls when positive biased by a torus output deflector, wherein the cylinder walls have maximum possible area for adsorption. Further the step of extracting the separated ribonucleic acid strands includes liberating RNA from the cylinder wall by negatively biasing a piezo-acoustic vibration agitator. The step of extracting the separated ribonucleic acid strands comprises recirculating the liquid travelling down the center of the cylinder by an RNA recirculation port. The step of extracting the separated ribonucleic acid strands includes progressively migrating RNA molecules towards output of the piezo electric type element, electrostatic ribonucleic acid extraction and concentration unit at high speed by a primary electrode, secondary electrode, and dosage electrode.

In another embodiment, a closed loop method of quality control of reverse transcriptase quantitative polymerase chain reaction analyzing system or any other chemistry undertaking biological assays whereby calibration data of the both the individual consumables and the measuring instrument are obtained and used. The method includes obtaining calibration data in the controlled environment of a purpose-designed manufacturing facility or the adaption of an existing one such as a pharmaceutical manufacturing facility, filling the individual consumables and sealing them within the controlled environment of the factory, storing the calibration data in both a non-volatile store that is a permanent component or attribute of the consumables and also storing it in an Internet-connected 'cloud' data storage facility such that the calibration data is obtainable for a specific consumable both locally in the test instrument and by way of quality control also to analytic systems such that parametric variation of the consumables and instrument may be compensated and corrected at the time of assay execution, and the closed environment of the consumables which excludes both contaminant ingress and pathogen egress as well as rendering harmless any pathogens in their volume and on their surface facilitates use without the attendance of clinically or scientifically-trained operatives permitting use in any environment and by any persons including the patients or clients themselves thus permitting the widest application and accessibility.

While specific language has been used to describe the disclosure, any limitations arising on account of the same are not intended. As would be apparent to a person skilled in the art, various working modifications may be made to the method in order to implement the inventive concept as taught herein.

The figures and the description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein. Moreover, the actions of any flow diagram need not be implemented in the order shown; nor do all of the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, and use of material, are possible.

What is claimed is:

1. A reverse transcriptase quantitative polymerase chain reaction based analyzing system comprising:
 a sampling tube comprising:
  a tube portion;
  a cap coupled to the tube portion via a ratchet locking mechanism, wherein the cap comprises a lens; and
  a radio frequency identification (RFID) tag disposed between the cap and the tube portion; and
 a microfluidic processing unit coupled to the sampling tube, wherein the microfluidic processing unit comprises:
  a piezo electric type element, electrostatic ribonucleic acid (RNA) extraction and concentration unit coupled to the sampling tube via a plurality of sample flow control devices;
  an eluent storage unit coupled to the piezo electric type element, electrostatic ribonucleic acid extraction and concentration (REC) unit via a plurality of eluent flow control devices;
  an eluate dosing chamber coupled to the REC unit via a plurality of eluate flow control devices;
  an analysis settling chamber coupled to the eluate dosing chamber;
  an assay rehydration unit coupled to the analysis settling chamber via a plurality of assay control devices;
  an assay analysis unit coupled to the analysis settling chamber; and
  a no-target control analysis unit coupled to the assay rehydration unit for the purposes of applying a negative control to the biological assay and simultaneously calibrating the optical metrology system by the provision of passive dyes that will be present in effectively the same quantities in both the no-target control and the biological sample, wherein the use of lyophilization in a factory to leave the required reagents in the allocated chambers of the microfluidic processing unit wherein the final stage of preparation prior to calibration involves displacing air in channels and chambers by argon in order to dispel oxygen that might otherwise facilitate gradual deterioration in the regents by oxidation.

2. The reverse transcriptase quantitative polymerase chain reaction based analyzing system as claimed in claim 1, wherein the REC unit comprises a high volume exit port and a low volume exit port.

3. The reverse transcriptase quantitative polymerase chain reaction based analyzing system as claimed in claim 2, wherein the REC unit is cylindrical and comprises an input deflector at inlet to direct material towards walls of the REC unit cylinder as it enters.

4. The reverse transcriptase quantitative polymerase chain reaction based analyzing system as claimed in claim 3, wherein the REC unit comprises a collar around and a wire passing through axial center of the cylinder.

5. The reverse transcriptase quantitative polymerase chain reaction based analyzing system as claimed in claim 4, wherein the REC unit comprises a torus output deflector to deflect material towards cylinder walls when positive biased, wherein the cylinder walls have maximum possible area for adsorption.

6. The reverse transcriptase quantitative polymerase chain reaction based analyzing system as claimed in claim 5, wherein the REC unit comprises a piezo-acoustic vibration agitator to assist eluent in liberating RNA from the cylinder walls when negative biased.

7. The reverse transcriptase quantitative polymerase chain reaction based analyzing system as claimed in claim 6, wherein the REC unit comprises an RNA recirculation port to recirculate the liquid travelling down the center of the cylinder.

8. The reverse transcriptase quantitative polymerase chain reaction based analyzing system as claimed in claim 7, wherein the REC unit comprises primary electrode, secondary electrode, and dosage electrode to progressively migrate RNA molecules towards output of the piezo electric type element, electrostatic ribonucleic acid extraction and concentration unit at high speed.

9. The reverse transcriptase quantitative polymerase chain reaction based analyzing system as claimed in claim 1, wherein act of closure of the cap is unidirectional and cannot be undone other than by destruction.

10. The reverse transcriptase quantitative polymerase chain reaction based analyzing system as claimed in claim 1, wherein closure of the tube is inspected by using the RFID tag.

11. The reverse transcriptase quantitative polymerase chain reaction based analyzing system as claimed in claim 1, wherein the assay analysis unit and the no-target control analysis unit are reaction chambers where a master mix of reagents, mix with extracted RNA.

12. The reverse transcriptase quantitative polymerase chain reaction based analyzing system as claimed in claim 11, wherein the reaction chambers include thermistors, heat pump, heat sink, mirror, and a lens mechanism.

13. The reverse transcriptase quantitative polymerase chain reaction based analyzing system as claimed in claim 11, comprising an optical subsystem, wherein the optical subsystem comprises one or more light sensors, filters, and a mirror integrated to the reaction chambers.

14. The reverse transcriptase quantitative polymerase chain reaction based analyzing system as claimed in claim 13, wherein the system is configured to reduce optical noise and biological noise, to improve signal to noise ratio.

15. A method for analyzing a biological sample, using a reverse transcriptase quantitative polymerase chain reaction analyzing system, the method comprising:

receiving a sample within a tube portion of a sampling tube;

coupling a cap of the sampling tube to the tube portion via a ratchet locking mechanism;

depositing a microfluidic laboratory comprising the sampling tube in an analytic cell (AC), wherein AC is an analytical process environment, wherein the AC may be just a single unit or may be one of a number assembled in a row; wherein a row of ACs, known as a RandOm-Access Analytical (RoaaaR) Array configured as one of a singular unit or one of many housed within an outer chassis, wherein the deposition is by way of either manual insertion or robotic assignment of individual sampling tubes and microfluidic laboratories into vacant ACs; wherein asynchronous, simultaneous processing of sampling tubes integrated with microfluidic laboratories whereby each sample test commences as it is inserted into an AC; wherein a control system to maintain asynchronism between assays in progress wherein optical metrology system is kept in constant use without delaying any given assay; wherein a signal detection mechanism using modulation of the excitation light correlated with both the spectrum and the intensity of individual wavelengths in the emission spectra to reduce electrical, electronic, optical and biological noise; wherein use of same modulation of the excitation light as a means of multiplexing by way of time division multiplexing (TDM) emissions from two or more ACs to economically use the same optical metrology system;

checking, by one or more detection sensors, the locking of the cap to the tube portion;

mixing a lysis buffer with the sample within the sampling tube to generate a lysated sample within the sampling tube via a mixing unit;

circulating the lysated sample from the sampling tube to a piezo electric type element, electrostatic ribonucleic acid extraction and concentration unit via a plurality of sample flow control devices;

separating ribonucleic acid strands from the lysated sample within the piezo electric type element, electrostatic ribonucleic acid extraction and concentration unit;

circulating an eluent between an eluent storage unit and the piezo electric type element, electrostatic ribonucleic acid extraction and unit;

extracting the separated ribonucleic acid strands, using the eluent from the piezo electric type element, electrostatic ribonucleic acid extraction unit and transferring an eluate comprising the extracted ribonucleic acid strands to an analysis settling chamber via an eluate dosing chamber and a plurality of eluate flow control devices;

mixing a portion of master mixture from an assay rehydration unit with the eluate within the analysis settling chamber;

transferring a first portion of the master mixture and the eluate to an assay analysis unit to analyze mixture of the portion of the master mixture and the eluate to diagnose a biological condition associated with the sample;

transferring a second portion of the master mixture from the assay rehydration unit to a no-target control analysis unit to perform a no-target control analysis of the second portion of the master mixture;

performing at least one of uniform (isothermal) or varying temperature control of the reverse transcriptase, quantitative polymerase chain reaction (RT-qPCR) assay or any other assay chemistry benefitting from the high accuracy, contaminant-free, optical detection methods;

providing asynchronous processing of the collection of simultaneous assays in a system to minimize the test extraction periods and share the more costly resources such as the optical subsystem between assays without slowing individual assays; and equipping individual microfluidic laboratories with mirrors underneath their reaction chambers to maximize the available emitted fluorescence, approximately doubling the light at each stage and for qPCR or RT-qPCR, reducing the cycle count by one.

16. The method for analyzing a biological sample as claimed in claim 15, wherein extracting the separated ribonucleic acid strands comprises deflecting material towards the cylinder walls when positive biased by a torus output deflector, wherein the cylinder walls have maximum possible area for adsorption.

17. The method for analyzing a biological sample as claimed in claim 15, wherein extracting the separated ribonucleic acid strands comprises liberating RNA from the cylinder wall by negatively biasing a piezo-acoustic vibration agitator.

18. The method for analyzing a biological sample as claimed in claim 15, wherein extracting the separated ribonucleic acid strands comprises recirculating the liquid travelling down the center of the cylinder by an RNA recirculation port.

19. The method for analyzing a biological sample as claimed in claim 15, wherein extracting the separated ribonucleic acid strands comprises progressively migrating RNA molecules towards output of the piezo electric type element, electrostatic ribonucleic acid extraction and concentration unit at high speed by a primary electrode, secondary electrode, and dosage electrode.

20. A closed loop method of quality control of reverse transcriptase quantitative polymerase chain reaction analyzing system or any other chemistry undertaking biological assays whereby calibration data of the both the individual consumables and the measuring instrument are obtained and used, the method comprising:

obtaining calibration data in the controlled environment of a purpose-designed manufacturing facility or the adaption of an existing one such as a pharmaceutical manufacturing facility;

filling the individual consumables and sealing them within the controlled environment of the factory;

storing the calibration data in both a non-volatile store that is a permanent component or attribute of the consumables and also storing it in an Internet-connected 'cloud' data storage facility such that the calibration data is obtainable for a specific consumable both locally in the test instrument and by way of quality control also to analytic systems such that parametric variation of the consumables and instrument may be compensated and corrected at the time of assay execution; and a closed environment of the consumables which excludes both contaminant ingress and pathogen egress as well as rendering harmless any pathogens in their volume and on their surface facilitates use without the attendance of clinically or scientifically-trained operatives permitting use in any environment and by any persons including the patients or clients themselves thus permitting the widest application and accessibility.

* * * * *